(12) United States Patent
Yang

(10) Patent No.: US 9,595,479 B2
(45) Date of Patent: Mar. 14, 2017

(54) METHOD AND STRUCTURE OF THREE DIMENSIONAL CMOS TRANSISTORS WITH HYBRID CRYSTAL ORIENTATIONS

(71) Applicant: MCube, Inc., San Jose, CA (US)

(72) Inventor: Xiao (Charles) Yang, Cupertino, CA (US)

(73) Assignee: mCube Inc., San Jose, CA (US)

( * ) Notice: Subject to any disclaimer, the term of this patent is extended or adjusted under 35 U.S.C. 154(b) by 82 days.

(21) Appl. No.: 14/218,633

(22) Filed: Mar. 18, 2014

(65) Prior Publication Data

US 2015/0270180 A1 Sep. 24, 2015
US 2017/0011972 A9 Jan. 12, 2017

Related U.S. Application Data

(63) Continuation-in-part of application No. 12/499,027, filed on Jul. 7, 2009, now Pat. No. 8,796,746, and a
(Continued)

(51) Int. Cl.
*H01L 31/036* (2006.01)
*H01L 21/8238* (2006.01)
(Continued)

(52) U.S. Cl.
CPC .. *H01L 21/823878* (2013.01); *B81C 1/00246* (2013.01); *G01L 9/0042* (2013.01);
(Continued)

(58) Field of Classification Search
CPC ......... H01L 21/02433; H01L 21/76254; H01L 27/0688; H01L 21/8221; H01L 21/823878;
(Continued)

(56) References Cited

U.S. PATENT DOCUMENTS 4,612,083 A 9/1986 Yasumoto et al.
5,090,963 A 2/1992 Gross et al.
(Continued)

OTHER PUBLICATIONS

Office Action for U.S. Appl. No. 12/634,634, mailed on Apr. 8, 2011, 15 pages.
(Continued)

*Primary Examiner* — Michael Trinh
(74) *Attorney, Agent, or Firm* — Kilpatrick Townsend & Stockton LLP

(57) ABSTRACT

A method for fabricating a three-dimensional integrated circuit device includes providing a first substrate having a first crystal orientation, forming at least one or more PMOS devices overlying the first substrate, and forming a first dielectric layer overlying the one or more PMOS devices. The method also includes providing a second substrate having a second crystal orientation, forming at least one or more NMOS devices overlying the second substrate, and forming a second dielectric layer overlying the one or more NMOS devices. The method further includes coupling the first dielectric layer to the second dielectric layer to form a hybrid structure including the first substrate overlying the second substrate.

18 Claims, 41 Drawing Sheets

Related U.S. Application Data continuation-in-part of application No. 13/311,538, filed on Dec. 5, 2011, now Pat. No. 8,704,238, which is a continuation of application No. 12/634,634, filed on Dec. 9, 2009, now Pat. No. 8,071,398, which is a continuation of application No. 12/499,029, filed on Jul. 7, 2009, now abandoned.

(60) Provisional application No. 61/079,112, filed on Jul. 8, 2008, provisional application No. 61/079,115, filed on Jul. 8, 2008, provisional application No. 61/079,116, filed on Jul. 8, 2008, provisional application No. 61/079,110, filed on Jul. 8, 2008, provisional application No. 61/079,113, filed on Jul. 8, 2008, provisional application No. 61/079,117, filed on Jul. 8, 2008, provisional application No. 61/084,223, filed on Jul. 28, 2008, provisional application No. 61/084,226, filed on Jul. 28, 2008.

(51) Int. Cl.

| | |
|---|---|
| *G01L 9/00* | (2006.01) |
| *H01L 21/762* | (2006.01) |
| *H01L 27/06* | (2006.01) |
| *H03H 3/007* | (2006.01) |
| *G01P 15/125* | (2006.01) |
| *G01P 15/08* | (2006.01) |
| *H01L 21/822* | (2006.01) |
| *B81C 1/00* | (2006.01) |
| *H01L 29/04* | (2006.01) |
| *H01L 25/065* | (2006.01) |
| *A61B 5/145* | (2006.01) |

(52) U.S. Cl.
CPC ........ *G01L 9/0054* (2013.01); *G01P 15/0802* (2013.01); *G01P 15/125* (2013.01); *H01L 21/76254* (2013.01); *H01L 21/8221* (2013.01); *H01L 27/0688* (2013.01); *H03H 3/0073* (2013.01); *A61B 5/14514* (2013.01); *B81B 2201/025* (2013.01); *B81B 2201/055* (2013.01); *H01L 25/0657* (2013.01); *H01L 29/045* (2013.01); *H01L 2924/0002* (2013.01)

(58) Field of Classification Search
CPC . H01L 25/0657; H01L 29/045; G01L 9/0054; G01L 9/0042; G01L 9/0073; B81C 1/00246; B81C 1/00238; B81C 1/0023; B81B 2201/025; B81B 2201/055
See application file for complete search history.

(56) References Cited

U.S. PATENT DOCUMENTS

| | | | |
|---|---|---|---|
| 5,135,499 A | 8/1992 | Tafani et al. | |
| 5,808,350 A | 9/1998 | Jack et al. | |
| 6,097,066 A | 8/2000 | Lee et al. | |
| 6,287,940 B1 | 9/2001 | Cole et al. | |
| 6,307,194 B1 | 10/2001 | Fitzgibbons et al. | |
| 6,393,913 B1 | 5/2002 | Dyck et al. | |
| 6,635,509 B1 | 10/2003 | Ouellet | |
| 6,821,826 B1* | 11/2004 | Chan et al. | 438/150 |
| 6,936,524 B2 | 8/2005 | Zhu et al. | |
| 7,091,057 B2 | 8/2006 | Gan et al. | |
| 7,402,449 B2* | 7/2008 | Fukuda | B81C 1/00246 257/415 |
| 7,470,957 B2 | 12/2008 | Gossner | |
| 7,536,769 B2 | 5/2009 | Pedersen | |
| 7,538,311 B2 | 5/2009 | Watanabe | |
| 7,709,896 B2 | 5/2010 | Russ et al. | |
| 7,885,423 B2 | 2/2011 | Weigold | |
| 7,887,508 B2 | 2/2011 | Meng et al. | |
| 7,943,412 B2 | 5/2011 | Buchwalter et al. | |
| 8,071,398 B1 | 12/2011 | Yang | |
| 8,148,781 B2 | 4/2012 | Yang | |
| 8,227,911 B1 | 7/2012 | Yang | |
| 8,704,238 B2 | 4/2014 | Yang | |
| 2001/0014516 A1* | 8/2001 | Shimoji | 438/458 |
| 2002/0039838 A1 | 4/2002 | Iida et al. | |
| 2002/0190210 A1 | 12/2002 | Ishikawa et al. | |
| 2004/0068224 A1 | 4/2004 | Couvillon et al. | |
| 2005/0067620 A1 | 3/2005 | Chan et al. | |
| 2005/0224714 A1 | 10/2005 | Akin et al. | |
| 2006/0087430 A1 | 4/2006 | Zambon | |
| 2006/0087717 A1 | 4/2006 | McGinley et al. | |
| 2006/0205106 A1 | 9/2006 | Fukuda et al. | |
| 2006/0244067 A1 | 11/2006 | Socher et al. | |
| 2006/0274399 A1 | 12/2006 | Yang | |
| 2007/0097487 A1 | 5/2007 | Yang et al. | |
| 2007/0218654 A1* | 9/2007 | Spencer et al. | 438/478 |
| 2008/0039792 A1 | 2/2008 | Meng et al. | |
| 2008/0283991 A1 | 11/2008 | Reinert | |
| 2009/0278217 A1 | 11/2009 | Laming et al. | |
| 2010/0075481 A1 | 3/2010 | Yang | |
| 2010/0164025 A1 | 7/2010 | Yang | |

OTHER PUBLICATIONS

Notice of Allowance for U.S. Appl. No. 12/634,634, mailed on Jul. 26, 2011, 7 pages.
Office Action for U.S. Appl. No. 13/311,538, mailed on Nov. 15, 2012, 6 pages.
Office Action for U.S. Appl. No. 13/311,538, mailed on Mar. 15, 2013, 6 pages.
Final Office Action for U.S. Appl. No. 13/311,538, mailed on Aug. 27, 2013, 10 pages.
Notice of Allowance for U.S. Appl. No. 13/311,538, mailed on Feb. 21, 2014, 5 pages.
Su et al., "A Resonant Accelerometer With Two-Stage Microleverage Mechanisms Fabricated by SOI-MEMS Technology," IEEE Sensors Journal vol. 5, No. 6, 2005, pp. 1214-1223.
Amantea et al., "An Uncooled IR Imager with 5 mK NEDT," SPIE vol. 3061, pp. 210-222, 1997.
Cole et al., "Monolithic Two-Dimensional Arrays of Micromachined Microstructures for Infrared Applications," Proceedings of the IEEE, vol. 86, No. 8, pp. 1679-1686, Aug. 1998.
Radford et al., "Microbolometer Uncooled Infrared Camera With 20 mK NETD," SPIE Conf. on Infrared Technology and Applications XXIV, SPIE vol. 3436, pp. 636-646, Jul. 1998.

\* cited by examiner

WLP 1st layer

Bondpad open (subsequent wafer bumping for BGA optional)

Alternative thinning method I
SOI

Alternative thinning method II
Implant and cleave

Thermal or mechanical cleave, followed by surface smoothing
Mech cleave has no diffusing issue 5. dep 2nd layer    a-Si, SOG, spay-on glass, metal, or combo
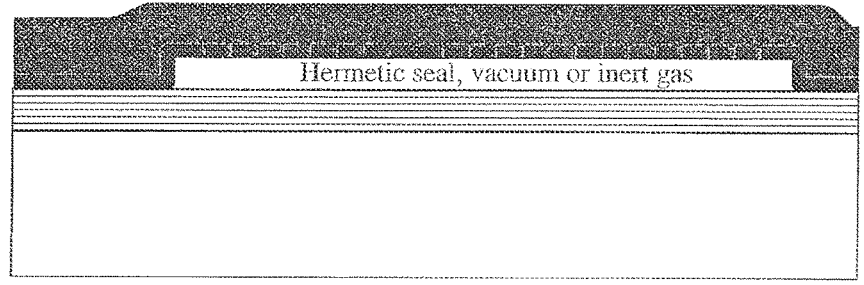
6. dep 3rd layer (optional)
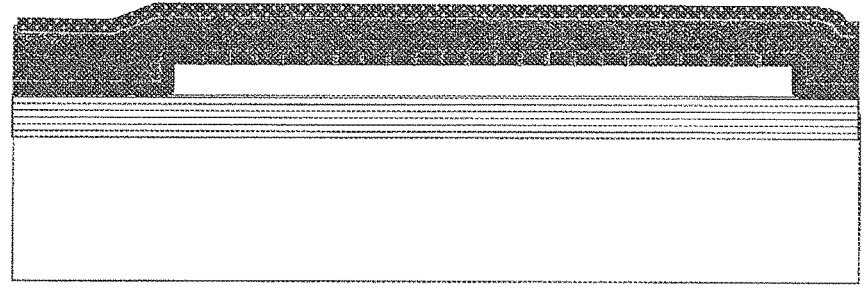
7. Bond pad opening
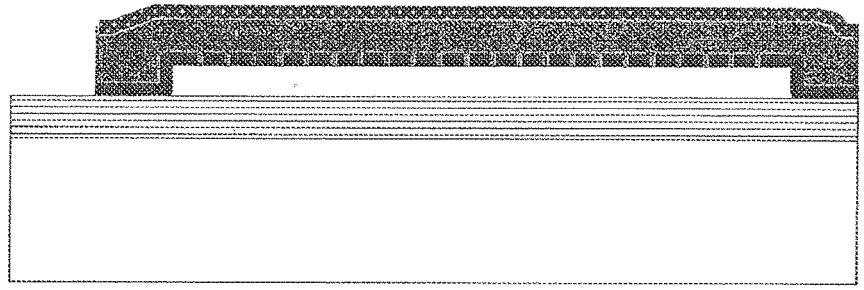
8. Wafer bumping (optional)
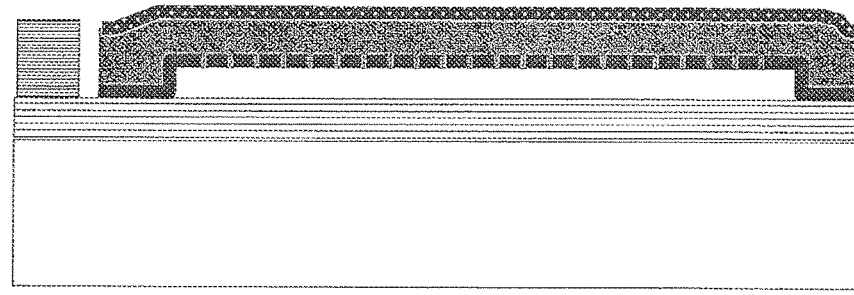
FIG. 24

1. dep 2$^{nd}$ layer
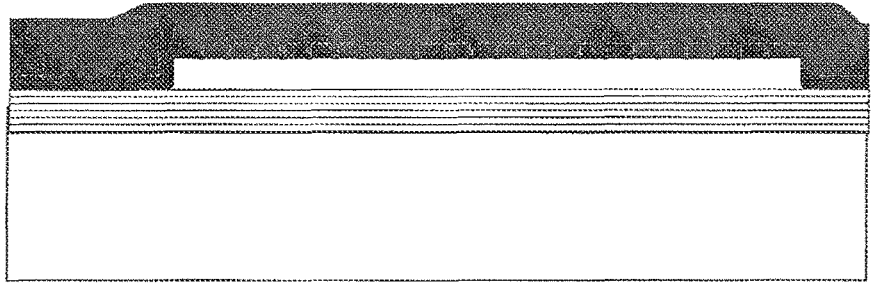
2. etch opening and expose bond pads
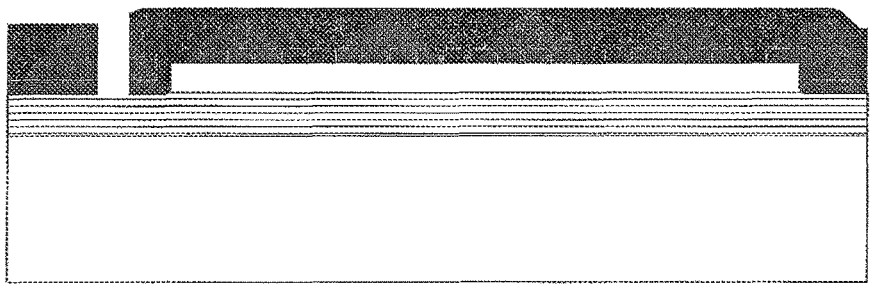
3. metalization
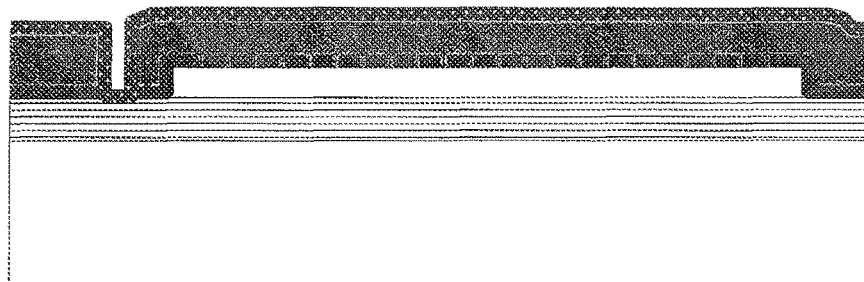
4. pattering metal, bond pads, or wafer bumping
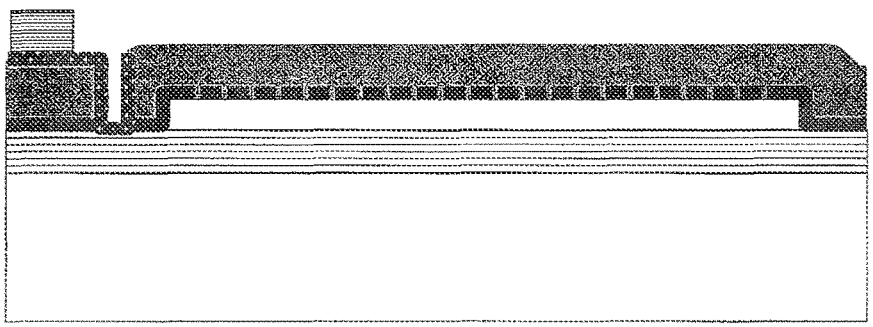
*FIG. 25*

1. Sacrificial material dep and pattern
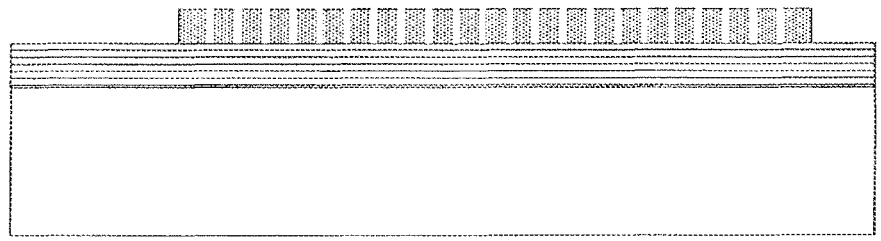
2. PVD 1st layer
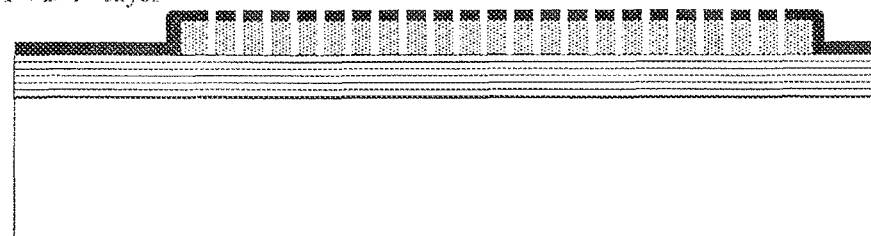
3. Remove sac
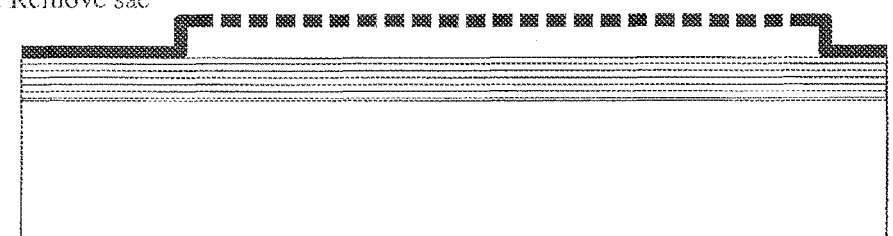
4. Dep 2nd layer    a-Si, SOG, spay-on glass, metal, or combo
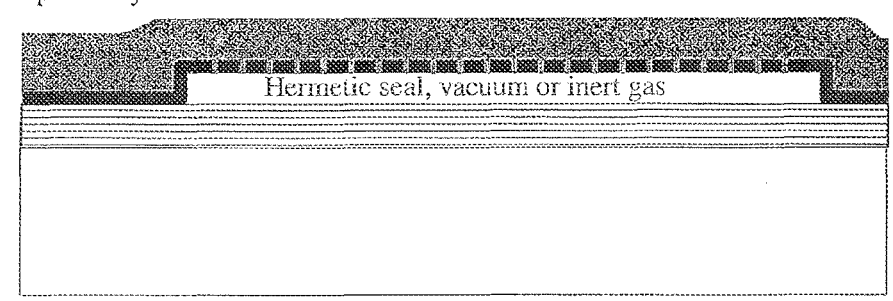
FIG. 26

|  | Incumbent | Simart | Simart Advantages |
|---|---|---|---|
| Anode | Graphite | Silicon nanopillar | • Silicon holds 10x Li than graphite: high energy density on the anode<br>• High surface area: fast charging and discharging |
| Cathode | LiCoO2 | Naopillar coated with LiCoO2 | • High surface area: more active material into the electrode, high energy capacity, fast charging and discharging |
| Separator | Thin plastic | Micromachined Silicon membrane with nanopillar | • Silicon is stronger than steel, avoid electrodes short that causes fire<br>• Nanopillar controls 'wetting' of electrolyte therefore physical contact/separation of electrodes<br>• Modularized control of nanopillar array allows intelligent battery operation for high efficiency<br>• No leakage, avoid deep discharge, extend battery life<br>• Silicon membrane potentially contains active IC for controlling battery |

*FIG. 29*

Battery "Off" state
Nanopillar charged, electrolyte separated from membrane
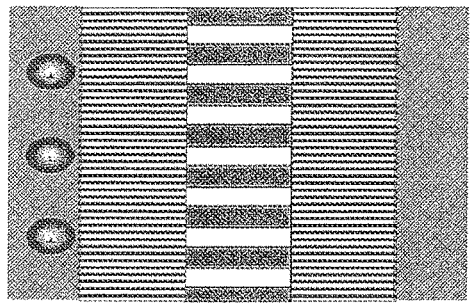
Battery partial "On" state
Part of nanopillar discharged, electrolyte immerse in membrane
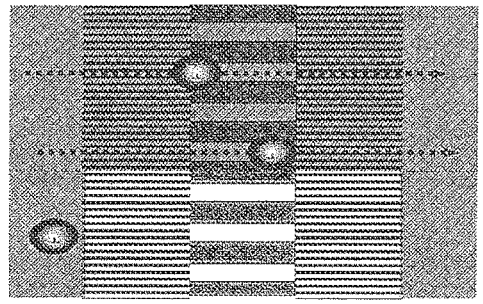
Battery fully "On" state
Nanopillar discharged, electrolyte immerse in membrane
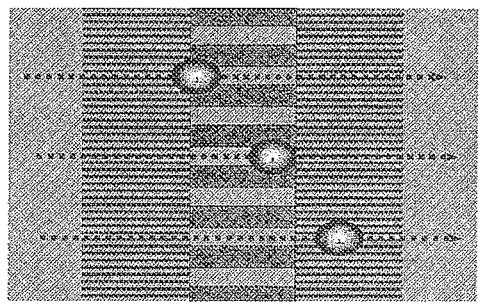
FIG. 31

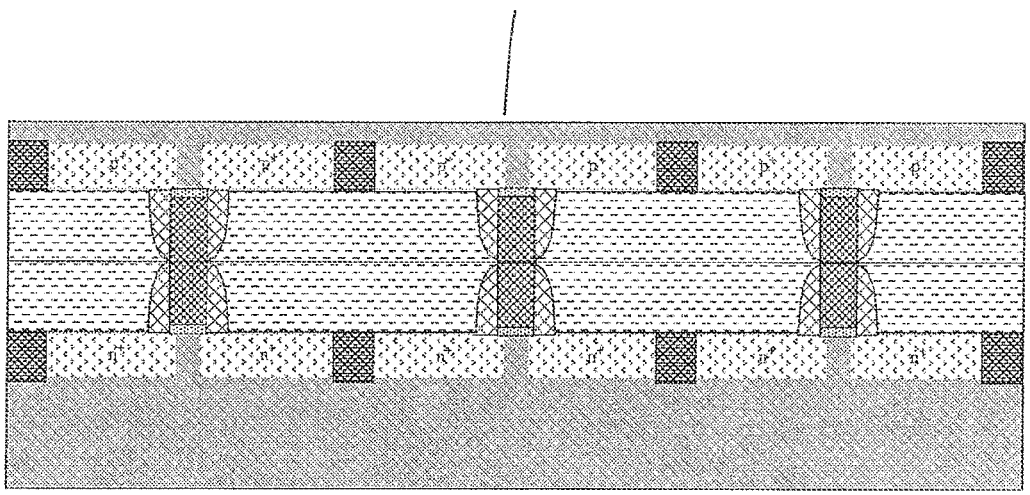
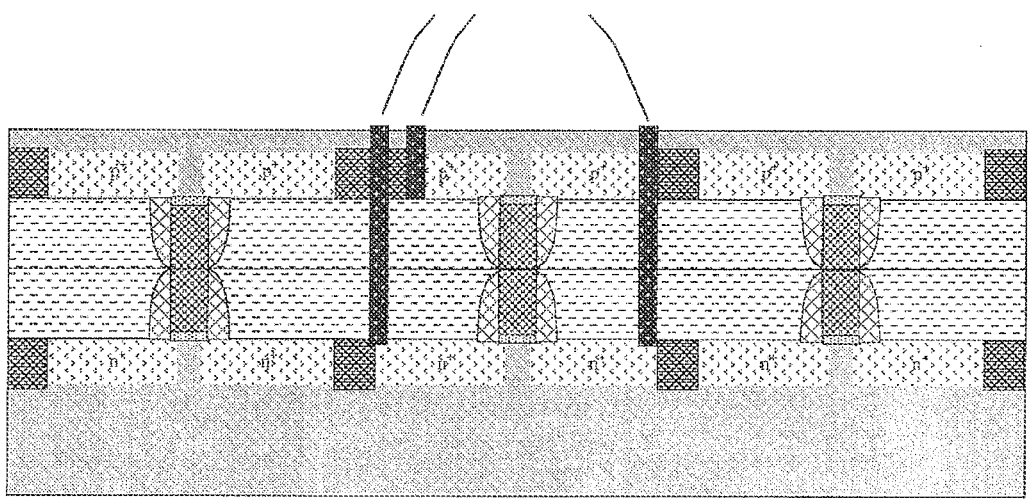
FIG. 36

Source & drain implant
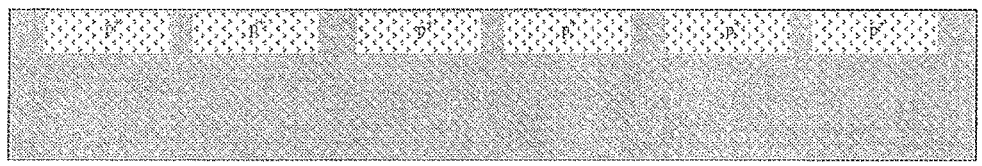
Gate oxide and poly
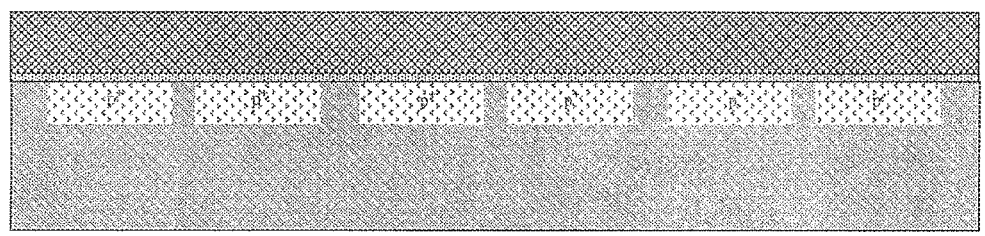
H2, He, Ar implant
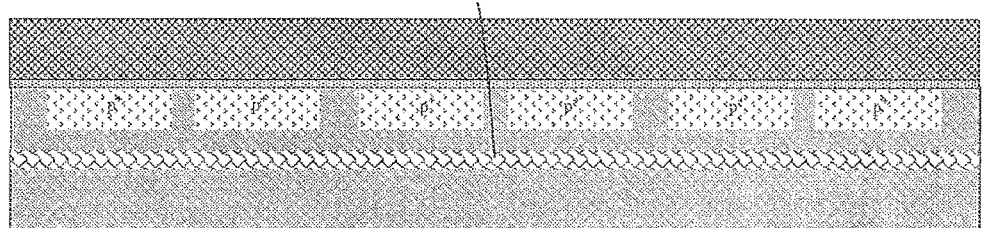
Transistor formation
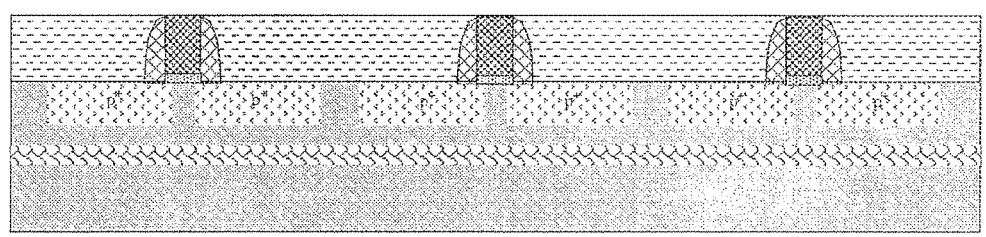
*FIG. 37*

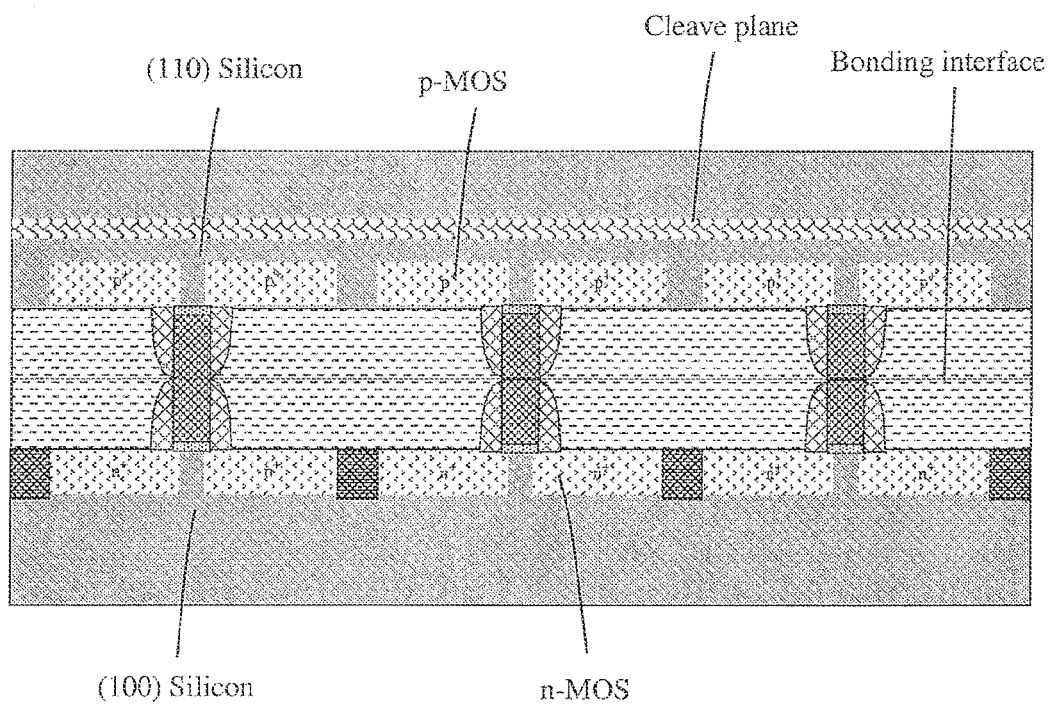
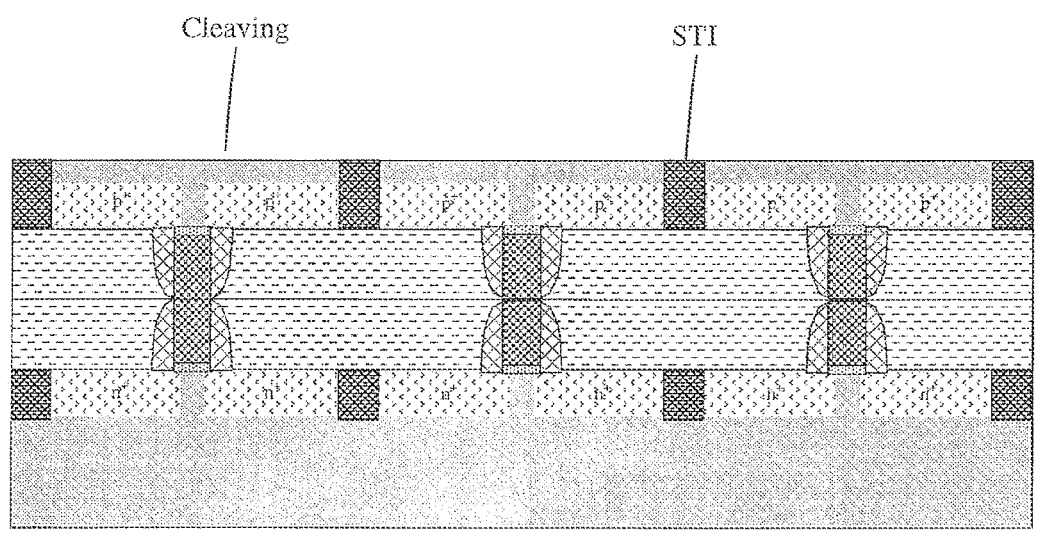
FIG. 38

METHOD AND STRUCTURE OF THREE DIMENSIONAL CMOS TRANSISTORS WITH HYBRID CRYSTAL ORIENTATIONS

CROSS-REFERENCES TO RELATED APPLICATIONS

This application is a continuation-in-part (CIP) application of U.S. patent application Ser. No. 12/499,027, filed Jul. 7, 2009, now U.S. Pat. No. 8,796,746, issued Aug. 5, 2014, which claims priority to U.S. Provisional Patent Application No. 61/079,112, filed Jul. 8, 2008, U.S. Provisional Patent Application No. 61/079,115, filed Jul. 8, 2008, and U.S. Provisional Patent Application No. 61/079,116, filed Jul. 8, 2008, all of which are commonly owned and are incorporated in their entirety herein by reference for all purposes. This application is a continuation-in-part (CIP) application of U.S. patent application Ser. No. 13/311,538, filed Dec. 5, 2011, now U.S. Pat. No. 8,704,238, issued Apr. 22, 2014, which is a continuation application of U.S. patent application Ser. No. 12/634,634, filed Dec. 9, 2009, which is a continuation application of U.S. patent application Ser. No. 12/499,029, filed Jul. 7, 2009, which claims priority to U.S. Provisional Patent Application No. 61/079,110, filed Jul. 8, 2008, U.S. Provisional Patent Application No. 61/079,113, filed Jul. 8, 2008, U.S. Provisional Patent Application No. 61/079,117, filed Jul. 8, 2008, U.S. Provisional Patent Application No. 61/084,223, filed Jul. 28, 2008, and U.S. Provisional Patent Application No. 61/084,226, filed Jul. 28, 2008, all of which are commonly owned and are incorporated in their entirety herein by reference for all purposes.

BACKGROUND OF THE INVENTION

The present invention is related to transistor devices. More particularly, the present invention provides a method and device for fabricating three-dimensional transistors with hybrid crystal orientations. Merely by way of example, the methods can be applied to CMOS, bipolar, diodes, etc.

Conventional transistors are fabricated on a surface of a silicon substrate, i.e. planar devices. A complementary metal-oxide-semiconductor (CMOS) device is a type of such planar devices that are typically fabricated side by side on a (100) silicon substrate. It is well known that electron mobility is highest for a (100) silicon surface with a <110> channel direction, while hole mobility is highest for a (110) silicon surface with a <110> channel direction.

Thus, it is desirable to fabricate a transistor device in a three dimensional manner with hybrid crystal orientation to improve density and performance of IC devices.

BRIEF SUMMARY OF THE INVENTION

The present invention relates to integrating a resonating mechanical device on top of an IC substrate monolithically using IC-foundry compatible processes. In an embodiment, the IC substrate is completed first using standard IC processes. A thick silicon layer is added on top of the IC. A subsequent patterning step defines a mechanical structure for resonating function. The mechanical device can be encapsulated by a thick insulating layer at the wafer level.

According to an embodiment of the present invention, a method for fabricating a monolithic integrated circuit and MEMS resonator device includes the following steps. The method includes providing a first semiconductor substrate having a first surface region and forming one or more CMOS integrated circuit device provided on a CMOS integrated circuit device region overlying the first surface region. The CMOS integrated circuit device region has a CMOS surface region. A dielectric layer is formed overlying the CMOS surface region. A second semiconductor substrate having a second surface region is joined to the CMOS surface region by bonding the second surface region to the dielectric layer. The second semiconductor substrate is thinned to a desired thickness while maintaining attachment to the dielectric layer. The method includes forming one or more via structures within one or more portions of the desired thickness of the second semiconductor substrate, and forming a conformal coating of metal material within the one or more via structures. The method also includes forming one or more free standing MEMS structures within one or more portions of the desired thickness of the second semiconductor substrate. The one or more MEMS structures are configured to be supported by one or more members integrally formed on the desired thickness of the second semiconductor substrate to cause the one or more MEMS structures to move in an oscillating manner characterized by a frequency range.

Compared with the incumbent bulk or surface micromachined MEMS inertial sensors, vertically monolithically integrated inertial sensors provided by embodiments of the present invention have one or more of the following advantages: smaller chip size, lower parasitics, higher sensitivity, lower power, and lower cost.

Using this architecture and fabrication flow, it is also feasible and cost-effective to make an array of resonators for multiple frequencies on a single chip.

Some embodiments of the present invention relate generally to integrated micro-machined and integrated circuit devices. More particularly, some embodiments of the present invention provide a sensing device integral with integrated circuits, such as CMOS integrated circuits, which are foundry compatible. These embodiments can be applied to a variety of applications, such as consumer, security, industrial, and medical.

Pressure sensors have been widely in industry. Conventional pressure sensors are used in consumer, industrial, and medical applications. Examples of consumer applications include gauges for tires, which are mounted on automobiles. Conventional bathroom type weight scales also use conventional pressure sensing devices. Industrial applications include pressure sensors in pipes for processing chemicals, oil, and semiconductor devices. Medical applications such as blood pressure monitors also rely upon conventional pressure sensing devices. Although highly successful and widely used, conventional pressure sensors have limitations in size, performance, and costs.

Specifically, conventional pressure sensors often use conventional micromachining techniques, common called "MEMS" techniques. Micromachined or MEMS pressure sensors are fabricated using bulk and surface micromachining techniques. Such bulk and surface machining techniques have limitations. That is, conventional bulk and surface machining techniques are often stand alone and are able to produce discrete MEMS based devices. Although highly successful, the MEMS based devices still have limitations. These and other limitations are described throughout the present specification and more particularly below.

Thus, it is desirable to have an improved MEMS device and more particularly pressure sensors.

Some embodiments of the present invention relate to integrating a MEMS pressure sensor on top of a CMOS substrate monolithically using IC-Foundry compatible processes. In some embodiments, the CMOS substrate is completed first using standard IC processes. A diaphragm is then added on top of the CMOS. In one embodiment, the diaphragm is made of deposited thin films with stress relief corrugated structure. In another embodiment, the diaphragm is made of a single crystal silicon material that is layer transferred to the CMOS substrate. In a specific embodiment, the integrated pressure sensor is encapsulated by a thick insulating layer at the wafer level. The monolithically integrated pressure sensor that adopts IC foundry-compatible processes yields the highest performance, smallest form factor, and lowest cost. The monolithically integrated pressure sensor can be used in a variety of applications, for example, for integrating a microphone device with signal processing and logic circuits.

In an embodiment, the present invention provides a pressure sensing device that includes a substrate having a surface region, a CMOS integrated circuit device layer overlying the surface region of the substrate, a diaphragm device having one or more surface regions overlying the CMOS integrated circuit device layer, and at least one or more spring devices spatially disposed within a vicinity of the one or more surface regions of the diaphragm device. Each of the folded spring devices is operably coupled to the one or more surface regions of the diaphragm device.

Other embodiments of pressure sensing devices and methods are described in more detail below.

Some embodiments of the present invention are related encapsulating integrated devices. More particularly, some of the embodiments of the present invention provide a method and device using CMOS fabrication techniques for encapsulating integrated circuits with cavity. For example, the encapsulation can be applied to RF integrated circuits, timing circuits, analog circuits, power circuits, SAW, FBAR, or any other semiconductor devices that are sensitive to ambient interference and changes.

High frequency integrated circuits such as RF and timing circuits are widely used in electronic applications to provide stable frequency selection or referencing. The stability of these circuits, however, is susceptible to EM interference, noise, moisture, corrosion, and gas from the environment.

Thus, it is desirable to improve the stability of timing circuits, RF circuits, and the like.

In an embodiment, an integrated circuits are completed using standard IC processes. A wafer-level hermetic encapsulation is applied to form a cavity above the sensitive portion of the circuits using IC-foundry compatible processes. The encapsulation and cavity provide a hermetic inert environment that shields the sensitive circuits from EM interference, noise, moisture, gas, and corrosion from the outside environment.

BRIEF DESCRIPTION OF THE DRAWINGS

FIG. 24 is a simplified process flow of a wafer-level encapsulation of integration circuits according to one embodiment of the present invention;

FIG. 25 is a simplified process flow of a wafer-level encapsulation of integration circuits according to one embodiment of the present invention;

FIG. 26 is a simplified process flow of a wafer-level encapsulation of Integration Circuits according to one embodiment of the present invention;

FIG. 29 is a simplified chart comparing silicon nanopillar battery to conventional battery according to one embodiment of the present invention;

FIG. 31 is a simplified diagram of operating modes of a silicon nanopillar battery according to one embodiment of the present invention;

FIG. 36 is a simplified diagram illustrating a process of thinning one of the transistor substrates;

FIGS. 37-38 are simplified diagrams illustrating a process of fabricating three dimensional transistor devices using a cleaving method according to an embodiment of the present invention;

DETAILED DESCRIPTION OF THE INVENTION

Figure 1:
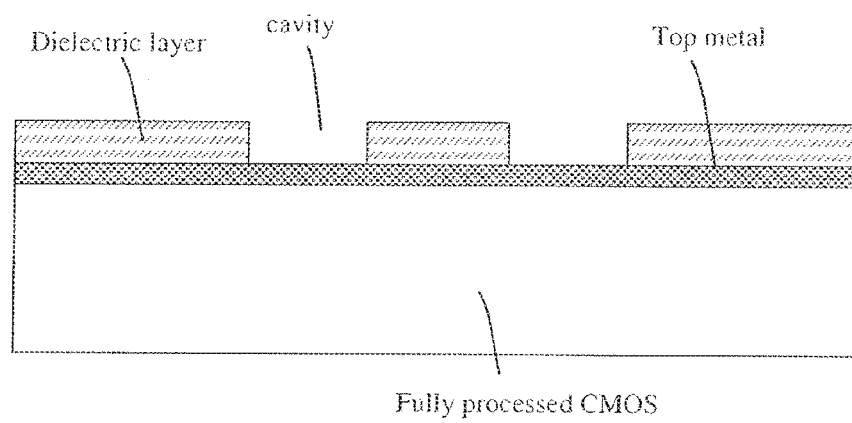
FIG. 1 is a simplified cross section diagram of components of a starting IC substrate according to one embodiment of the present invention.

FIG. 1 is a simplified cross section diagram of components of a starting IC substrate according to one embodiment of the present invention. As depicted, the starting substrate is a fully processed IC wafer. A dielectric layer such as oxide and nitride is deposited on top of a top metal layer of the IC wafer. The dielectric layer is then patterned to form a structure that provides anchor points for stationary members of the mechanical resonating device.

Figure 2:
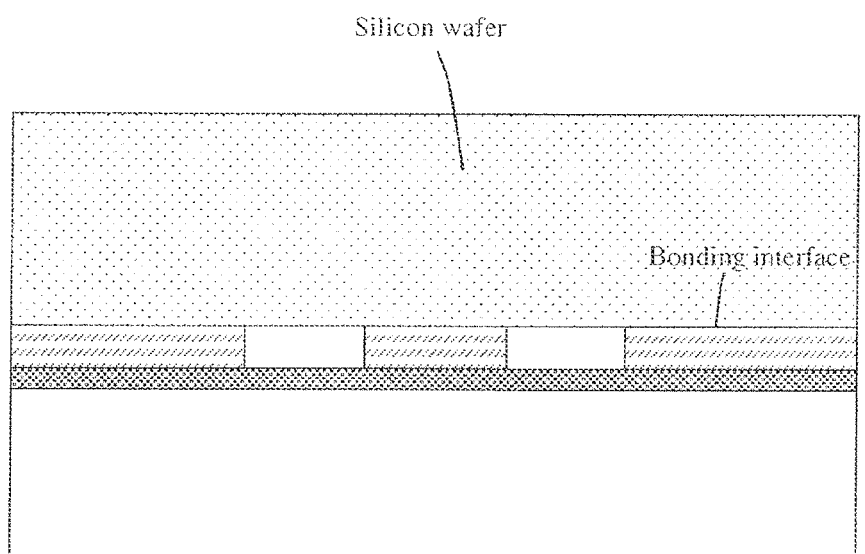
FIG. 2 is a simplified cross section diagram of components of a monolithically integrated inertial sensing device according to one embodiment of the present invention.

FIG. 2 is a simplified cross section diagram of components of a monolithically integrated inertial sensing device according to one embodiment of the present invention. As depicted, a silicon wafer is bonded to the IC substrate. The bonding methods include but not limited to: covalent, Spin-on-glass (SOG), Eutectic, and anodic. The bonding temperature is IC compatible and below 400 C.

Figure 3:
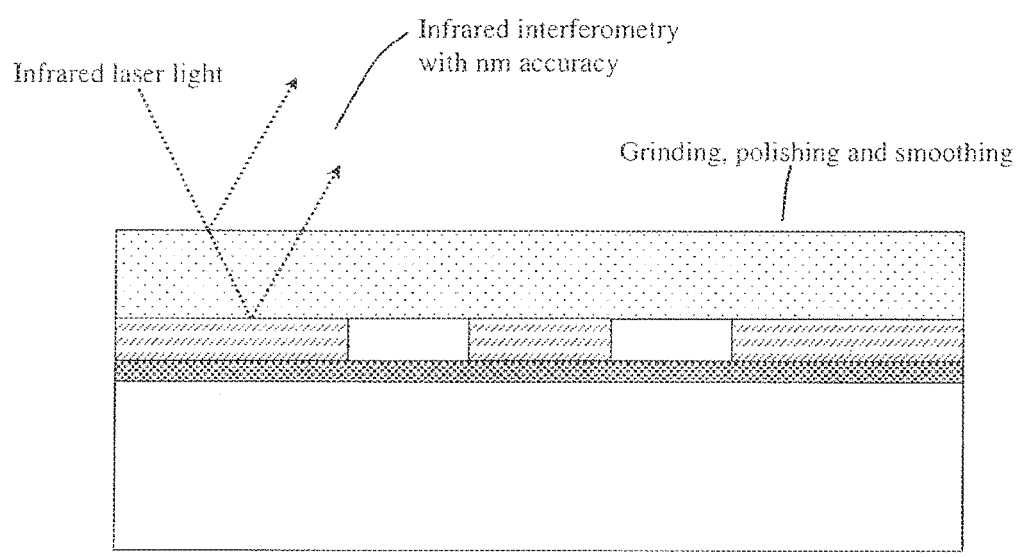
FIG. 3 is a simplified cross section diagram of components of a monolithically integrated inertial sensing device according to one embodiment of the present invention.

FIG. 3 is a simplified cross section diagram of components of a monolithically integrated inertial sensing device according to one embodiment of the present invention. As depicted, the silicon substrate is thinned by techniques such as grinding, polishing, and etching. The final thickness of the remaining silicon atop of the IC is precisely measured by infrared interferometry method with nano meter accuracy. Infrared wavelength is used because silicon is transparent in this spectrum.

Figure 4:
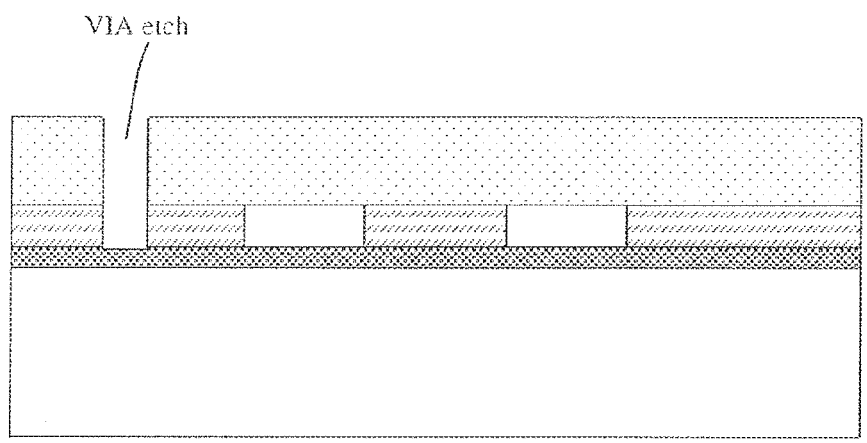
FIG. 4 is a simplified cross section diagram of components of a monolithically integrated inertial sensing device according to one embodiment of the present invention.

FIG. 4 is a simplified cross section diagram of components of a monolithically integrated inertial sensing device according to one embodiment of the present invention. As depicted, a VIA hole is etched into the silicon and top dielectric layers and stop on the top metal layer. The size of the VIA ranges from 0.5 um to a few micro meters depending on the thickness of the silicon layer. The profile or sidewall of the VIA is tapered or slopped for better step coverage of subsequent metallization step.

Figure 5:
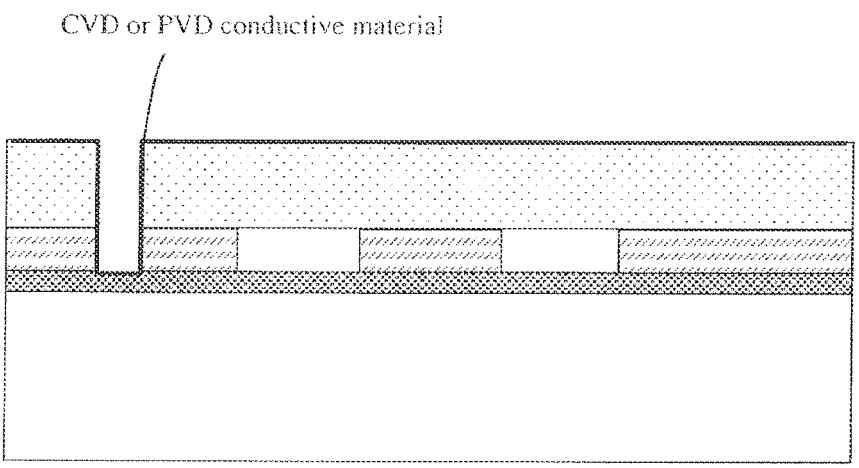
FIG. 5 is a simplified cross section diagram of components of a monolithically integrated inertial sensing device according to one embodiment of the present invention.

FIG. 5 is a simplified cross section diagram of components of a monolithically integrated inertial sensing device according to one embodiment of the present invention. As depicted, a metal layer is blanket deposited on the wafer covering the silicon surface as well as the VIA surface. CVD or PVD recipes are optimized to achieve good step coverage of the VIA as well as low stress of the metal film. In one embodiment, the metal layer is a CVD TiN material that has excellent step coverage of the VIA. The thickness of the metal ranges from a few hundreds of angstroms to a few micro meters depending the applications requirements. An optional electroplating step can be used to fill the entire VIA with metals such as Copper or Nickel.

Figure 6:
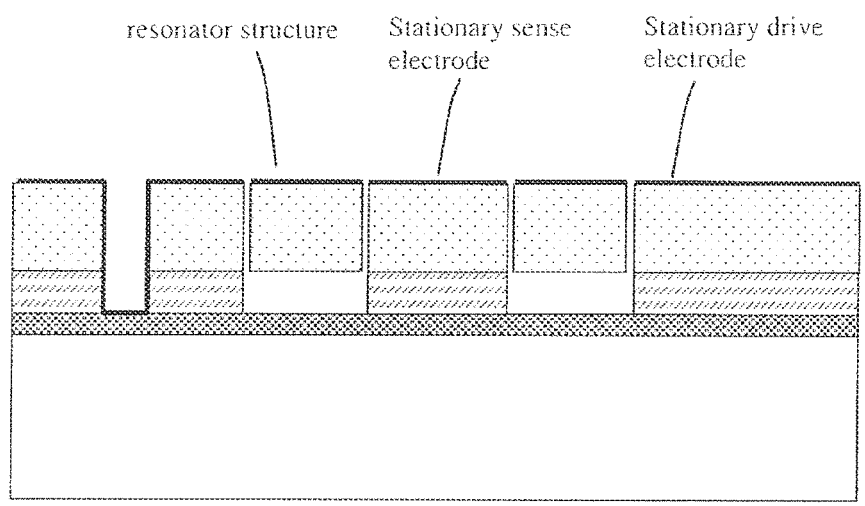
FIG. 6 is a simplified cross section diagram of components of a monolithically integrated inertial sensing device according to one embodiment of the present invention.

FIG. 6 is a simplified cross section diagram of components of a monolithically integrated inertial sensing device according to one embodiment of the present invention. As depicted, the silicon layer is patterned typically by a DRIE step. The patterned mechanical structure includes one or more freestanding members and stationary electrodes that are anchored to the top oxide. The freestanding members have desired stiffness/compliance that determines the resonate frequency of the mechanical resonator. The stationary drive electrodes couple to the freestanding member electrostatically. The freestanding member oscillates when applying a periodically voltage waveform between the freestanding member and the drive electrodes. The movement cause a change in capacitance between the movable freestanding member and stationary sense electrodes. The capacitance change is detected by the integrated circuits a few micrometer below and fed back to the drive electrodes to keep the freestanding member oscillating at its resonate frequency.

Figure 7:
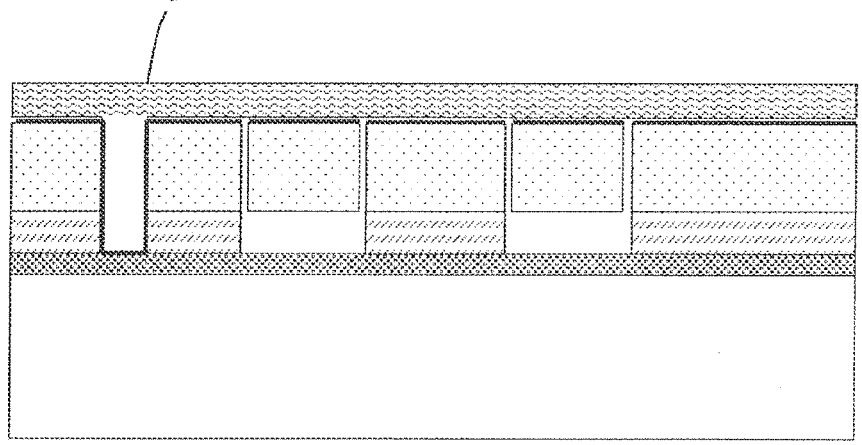
FIG. 7 is a simplified cross section diagram of components of a monolithically integrated inertial sensing device according to one embodiment of the present invention.

FIG. 7 is a simplified cross section diagram of components of a monolithically integrated inertial sensing device according to one embodiment of the present invention. As depicted, an organic sacrificial material is deposited covering the mechanical structure. In one embodiment, the sacrificial material is a liquid photo resist that is spin coated on the wafer and fill all the VIA holes and trenches. In another embodiment, the sacrificial material is a dry film photoresist that is deposited on the surface of the wafer and does not fill the holes and trenches.

Figure 8:
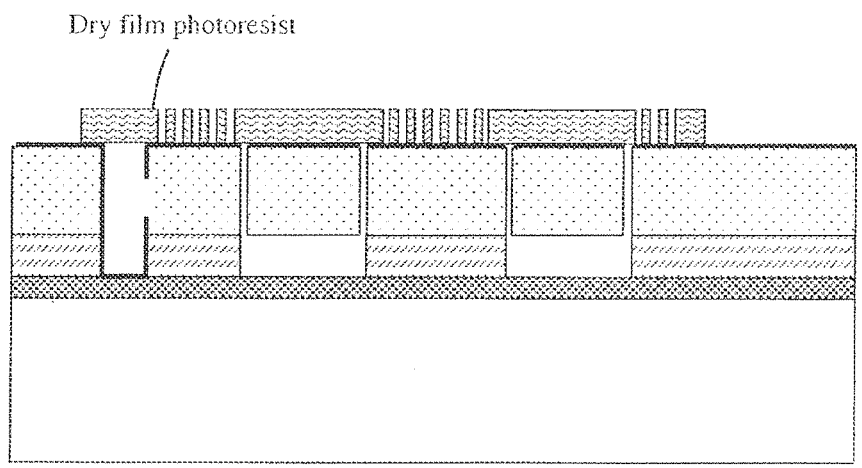
FIG. 8 is a simplified cross section diagram of components of a monolithically integrated inertial sensing device according to one embodiment of the present invention.

FIG. 8 is a simplified cross section diagram of components of a monolithically integrated inertial sensing device according to one embodiment of the present invention. As depicted, the photo resist is patterned by an exposure and develop lithography process. The exposed area are non-trench features such as proof mass and anchors.

Figure 9:
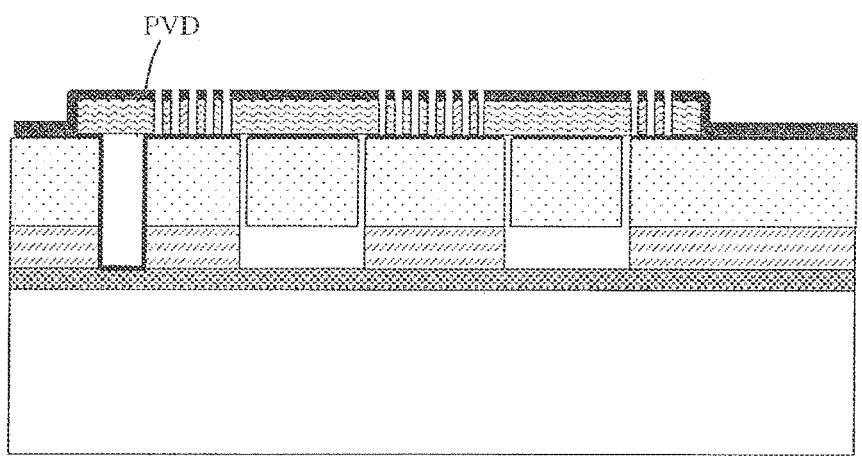
FIG. 9 is a simplified cross section diagram of components of a monolithically integrated inertial sensing device according to one embodiment of the present invention.

FIG. 9 is a simplified cross section diagram of components of a monolithically integrated inertial sensing device according to one embodiment of the present invention. As depicted, the $1^{st}$ layer of the encapsulation is deposited by a PVD process. The deposition recipe is optimized for non-conforming purpose, which has little step coverage of the sidewall of the exposed photoresist trenches.

Figure 10:
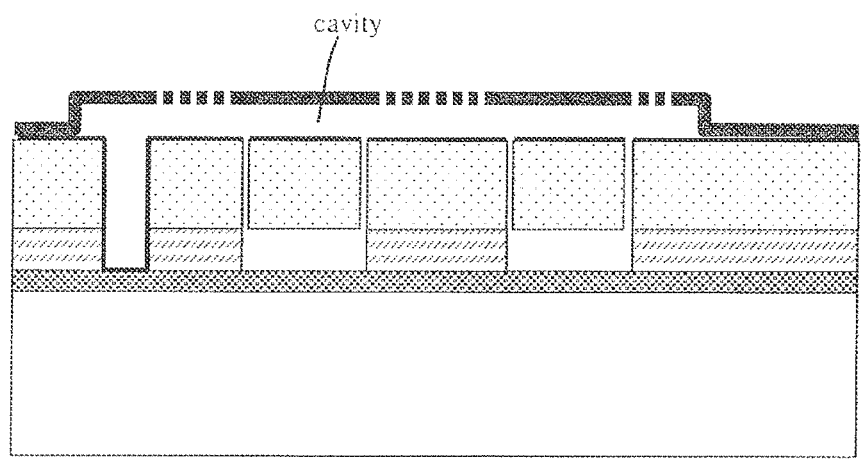
FIG. 10 is a simplified cross section diagram of components of a monolithically integrated inertial sensing device according to one embodiment of the present invention.

FIG. 10 is a simplified cross section diagram of components of a monolithically integrated inertial sensing device according to one embodiment of the present invention. As depicted, the sacrificial organic material is then removed by a dry O2 plasma ashing step. The removal of the sacrificial material releases the sensor device and forms the 1$^{st}$ shell of the encapsulation.

Figure 11:
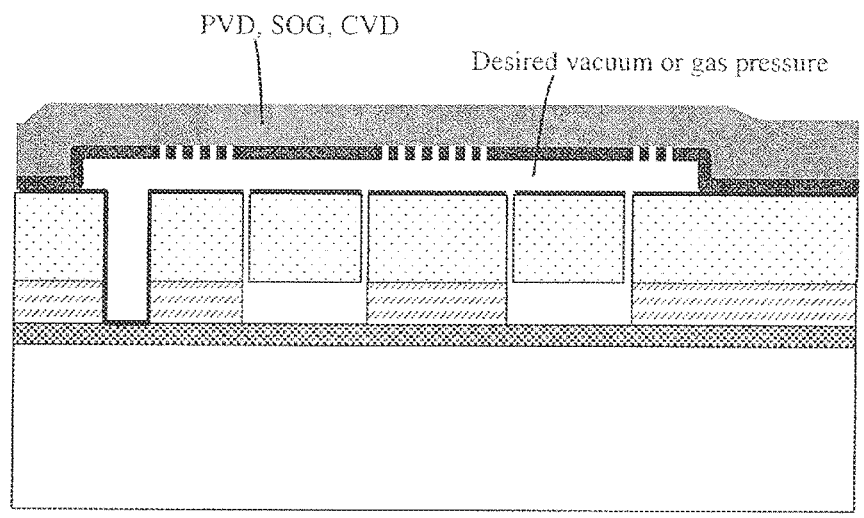
FIG. 11 is a simplified cross section diagram of components of a monolithically integrated inertial sensing device according to one embodiment of the present invention.

FIG. 11 is a simplified cross section diagram of components of a monolithically integrated inertial sensing device according to one embodiment of the present invention. As depicted, the 2$^{nd}$ layer of the encapsulation is deposited onto the 1$^{st}$ layer. The sealing methods include PVD, spin-on, or spray-on techniques. The sealing materials include metal such as Ti, TiN, amorphous silicon, spin-on-glass, spray-on-glass, or a combination of the above. The ambient during sealing is optimized to achieve the highest vacuum level possible after sealing. A getter material such as Ti can be deposited as the 1$^{st}$ layer of the encapsulation and activated later to achieve higher vacuum and cleanness of the ambient environment. After sealing the holes, an optional CVD dielectric material such as oxide or nitride can be added onto the encapsulation.

Figure 12:
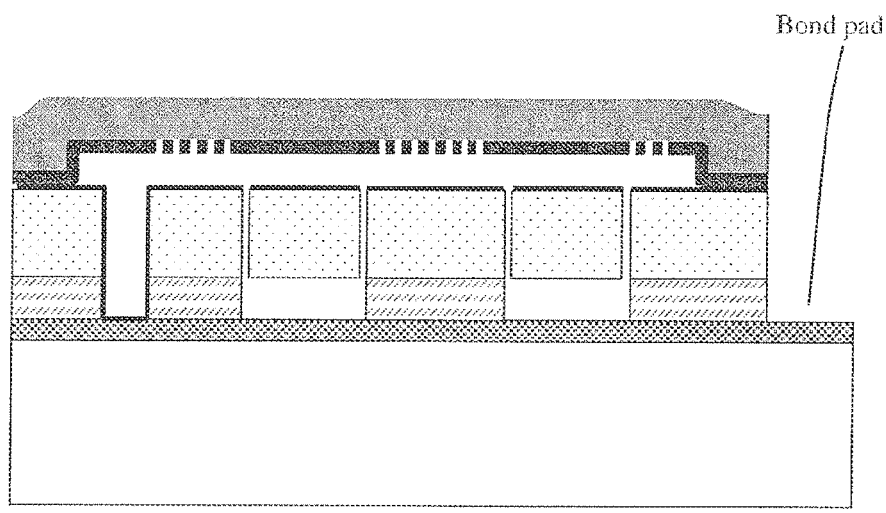
FIG. 12 is a simplified cross section diagram of components of a monolithically integrated inertial sensing device according to one embodiment of the present invention.

FIG. 12 is a simplified cross section diagram of components of a monolithically integrated inertial sensing device according to one embodiment of the present invention. As depicted, a etch step opens the bond pad area and expose the bond pads for wire bonding or optional wafer bumping processes.

Figure 13A:
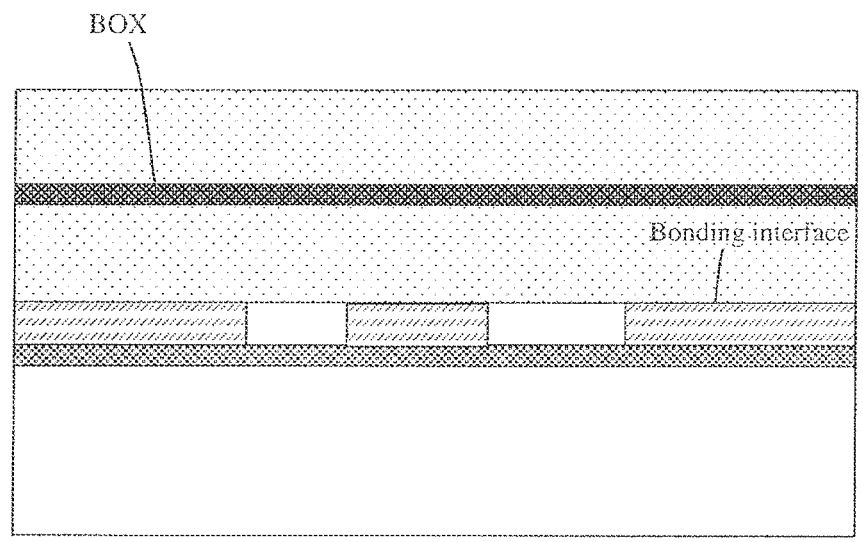
FIGS. 13A and 13B are simplified cross section diagrams of an alternative method of controlling silicon layer thickness of a monolithically integrated inertial sensing device according to one embodiment of the present invention.
Figure 13B:
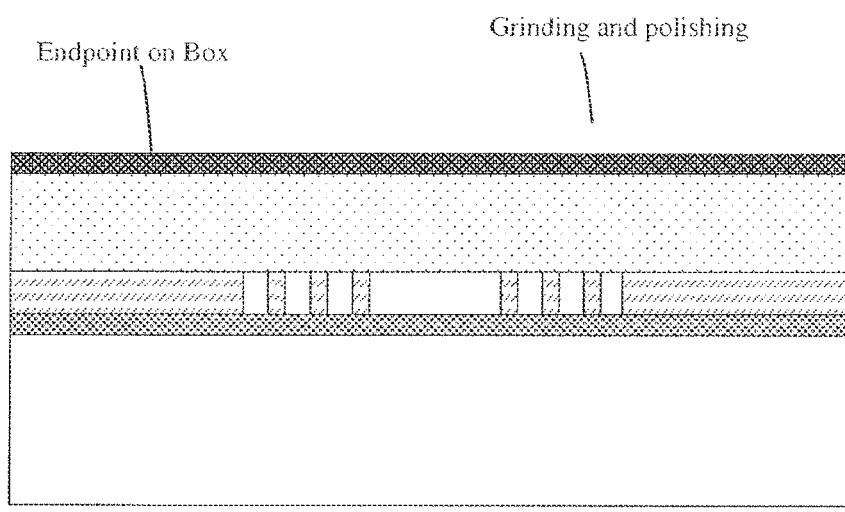

FIGS. 13A and 13B are simplified cross section diagrams of an alternative method of controlling silicon layer thickness of a monolithically integrated inertial sensing device according to one embodiment of the present invention. As depicted in FIG. 13A, the blanket silicon wafer is a SOI wafer with a desired SOI thickness. As illustrated in FIG. 13B, the BOX of the SOI provides an etch stop during the thinning process steps. The BOX can be then used as a hard mask to define the sensor structure.

Figure 14A:
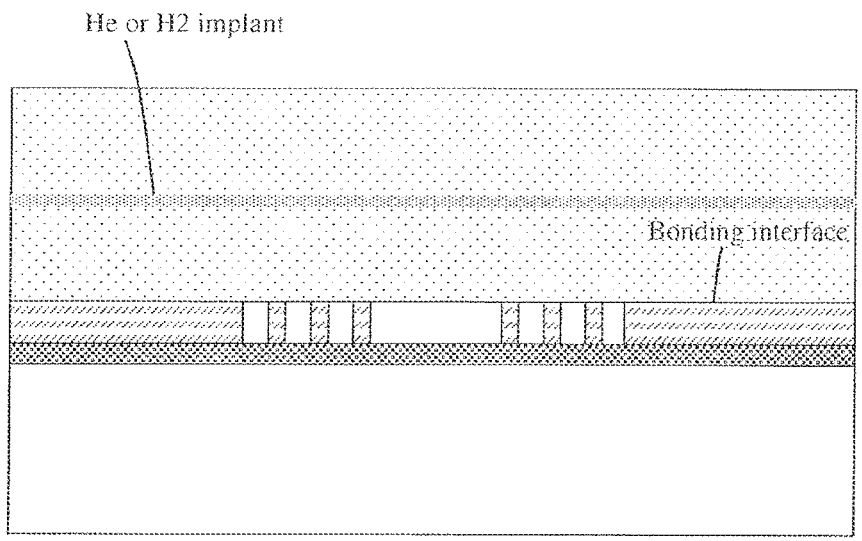
FIGS. 14A and 14B are simplified cross section diagrams of an alternative method of controlling silicon layer thickness of a monolithically integrated inertial sensing device according to one embodiment of the present invention.
Figure 14B:
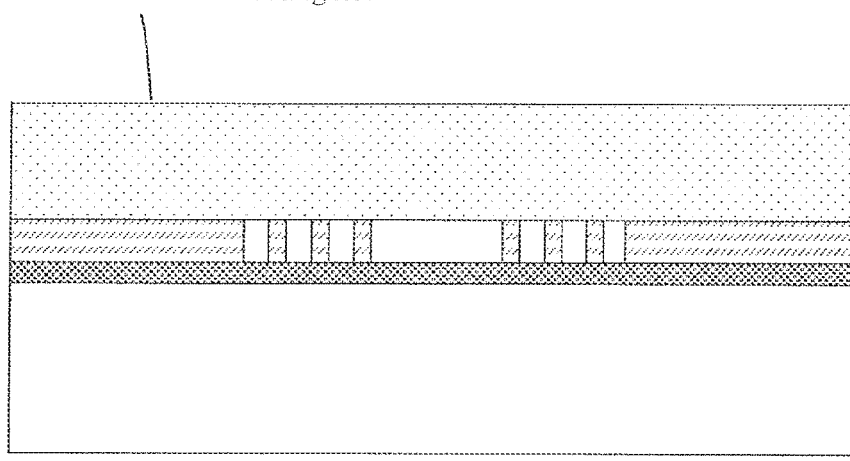

FIGS. 14A and 14B are simplified cross section diagrams of an alternative method of controlling silicon layer thickness of a monolithically integrated inertial sensing device according to one embodiment of the present invention. As depicted in FIG. 14A, the blanket silicon wafer has a layer of implanted H2, He, or Ar in a desired thickness in the silicon substrate. As illustrated in FIG. 14B, this thickness of silicon is separated from the bulk at the implant layer. Separation methods include thermal cleave and mechanical cleave. A subsequent polishing or etching step smoothens the cleaved surface of the remaining silicon layer.

According to an embodiment of the present invention, a method for fabricating a monolithic integrated circuit and MEMS resonator device includes the following steps. The method includes providing a first semiconductor substrate having a first surface region and forming one or more CMOS integrated circuit device provided on a CMOS integrated circuit device region overlying the first surface region. The CMOS integrated circuit device region has a CMOS surface region. A dielectric layer is formed overlying the CMOS surface region. A second semiconductor substrate having a second surface region is joined to the CMOS surface region by bonding the second surface region to the dielectric layer. The second semiconductor substrate is thinned to a desired thickness while maintaining attachment to the dielectric layer. The method includes forming one or more via structures within one or more portions of the desired thickness of the second semiconductor substrate, and forming a conformal coating of metal material within the one or more via structures. The method also includes forming one or more free standing MEMS structures within one or more portions of the desired thickness of the second semiconductor substrate. The one or more MEMS structures are configured to be supported by one or more members integrally formed on the desired thickness of the second semiconductor substrate to cause the one or more MEMS structures to move in an oscillating manner characterized by a frequency range.

In an embodiment of the above method, the dielectric layer has one or more patterned regions. In another embodiment, the thinning includes a grinding process to remove a thickness of material from the semiconductor substrate to expose a ground surface region and further includes subjecting the ground surface region to a polishing process to smooth the ground surface region to a predetermined surface roughness; and monitoring a thickness of the second substrate during either or both the grinding process and/or the polishing process.

In another embodiment, the monitoring includes using an interferometer process to measure an indication associated with the thickness of the second substrate, the interferometer process using a electromagnetic radiation in an infrared wavelength range.

In another embodiment, the method also includes forming one or more via structures within one or more portions of the second semiconductor substrate. The one or more via structures extend from the second surface region to a vicinity of the desired thickness. The one or more via structures are configured as one or more stop structures to form one or more end point regions of the thinning.

In another embodiment, the second semiconductor substrate is an SOI substrate having a bulk portion, overlying insulating layer, and single crystal device layer. The thinning includes selectively removing the bulk portion of the SOI substrate from the single crystal device layer while maintaining attachment to the dielectric layer.

In another embodiment, the thinning includes cleaving a portion of the second semiconductor substrate at a cleave region to remove the desired thickness from the second semiconductor substrate. The cleave region is within a vicinity of the desired thickness, which is a remaining portion of the second semiconductor substrate attached to the dielectric layer.

In another embodiment, the one or more free standing MEMS structures includes one or more comb structures, each of the comb structures being configured to be movable from a first position to a second position. At least one of the comb structures is inter-digitated with a second comb structure, which is stationary.

In another embodiment, the one comb structure and the second comb structure form a capacitive sensing device, which is capable of providing a varying capacitance upon movement of the one or more free standing MEMS structures responding to external acceleration.

In another embodiment, the CMOS device layer is formed using a standing CMOS process from a semiconductor foundry.

In another embodiment, the method also includes forming a sacrificial layer overlying the one or more free standing MEMS structures.

In another embodiment, the method also includes forming an enclosure layer overlying the sacrificial layer. The enclosure layer has one or more openings to expose one or more portions of the sacrificial layer.

In another embodiment, the enclosure layer includes a titanium material, the titanium material being activated as a getter layer.

In another embodiment, the enclosure layer is selected from a metal, a semiconductor material, an amorphous silicon material, a dielectric layer, or a combination of these layers.

In another embodiment, the method also includes removing the sacrificial layer via an ashing process to form an open region between the one or more free standing MEMS structures and the enclosure layer and forming an encapsulating layer overlying the enclosure layer to substantially seal the one or more free standing MEMS structures to form a predetermined environment within the open region.

In another embodiment, the encapsulating layer is selected from a metal layer, a spin on glass, spray on glass, amorphous silicon, a dielectric layer, or any combination of these layers.

In another embodiment, the frequency range is radio frequency range from kilo-hertz to giga-hertz.

In another embodiment, the method also includes forming one or more bond pad openings to expose one or more of bond pads coupled to the CMOS device layer.

According to an alternative embodiment, the invention provides a method of forming a monolithic MEMS and integrated circuit device. The method includes providing a first semiconductor substrate having a first surface region and forming one or more CMOS integrated circuit device provided on a CMOS integrated circuit device region overlying the first surface region. The CMOS integrated circuit device region has a CMOS surface region. The method also includes forming a dielectric layer overlying the CMOS surface region, and joining a second semiconductor substrate having a second surface region to the CMOS surface region by bonding the second surface region to the dielectric layer. The second semiconductor substrate includes a bulk substrate, an overlying insulating layer, and a single crystal device layer which includes the second surface region. The method also includes thinning the second semiconductor substrate to a desired thickness including the single crystal device layer, the insulating layer, and a portion of the bulk substrate while maintaining attachment to the dielectric layer. The method also includes forming one or more MEMS structures within one or more portions of the desired thickness of the second semiconductor substrate. The one or more MEMS structures are configured to be supported by one or more members integrally formed on the desired thickness of the second semiconductor substrate to cause the one or more MEMS structures to move in an oscillating manner characterized by a frequency range.

Figure 15:
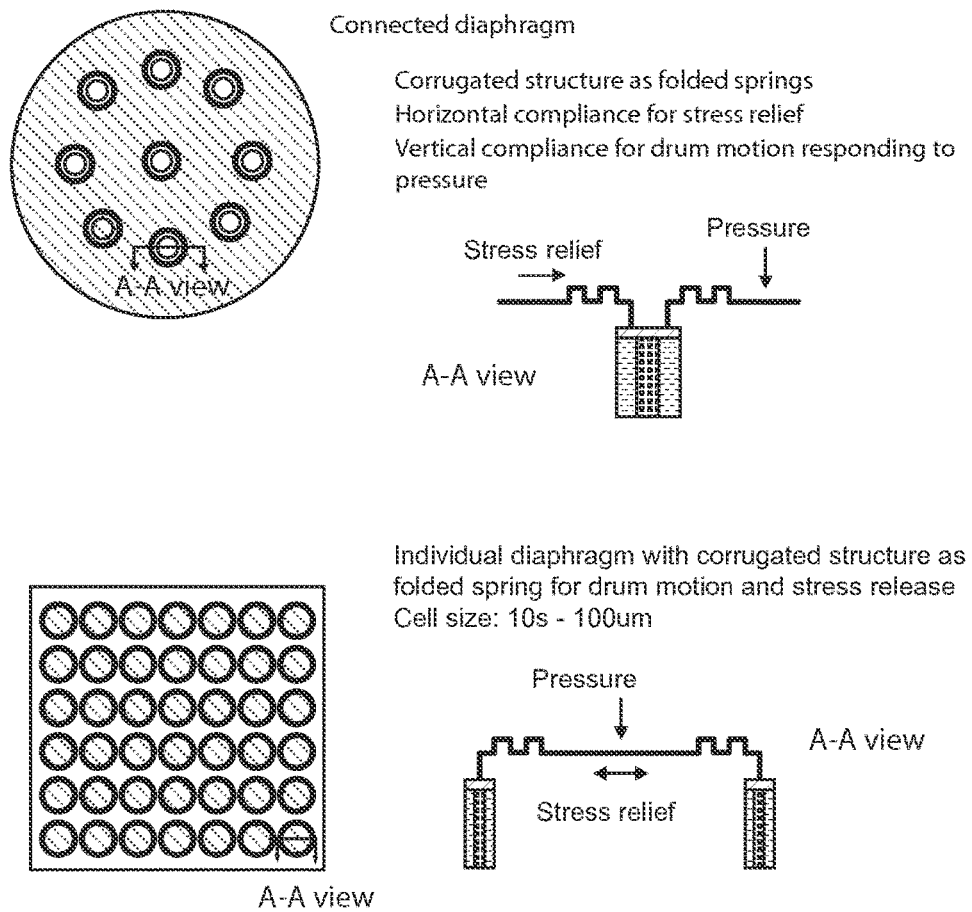
FIG. 15 is a simplified diagram of components of a micromachined pressure sensor according to one embodiment of the present invention.

FIG. 15 is a simplified diagram of components of a micromachined pressure sensor according to one embodiment of the present invention. As depicted, the diaphragm is either a continuous layer or an array of smaller diaphragm cells. To obtain high sensitivity of the microphone, a large and thin diaphragm is essential. It is, however, difficult to achieve due to intrinsic stress of the diaphragm film. As shown in the cross section view, a corrugated structure is adopted as folded springs. The folded spring has a horizontal compliance that is used for stress relief of the diaphragm film. The folder spring also has a vertical compliance that is used for drum motion responding to a sound pressure. In the continuous diaphragm configuration, the corrugated structures are evenly distributed with local supporting posts. In the array configuration, the diaphragm in each cell has corrugated structures at the edge and is anchored at the perimeter.

Figure 16:
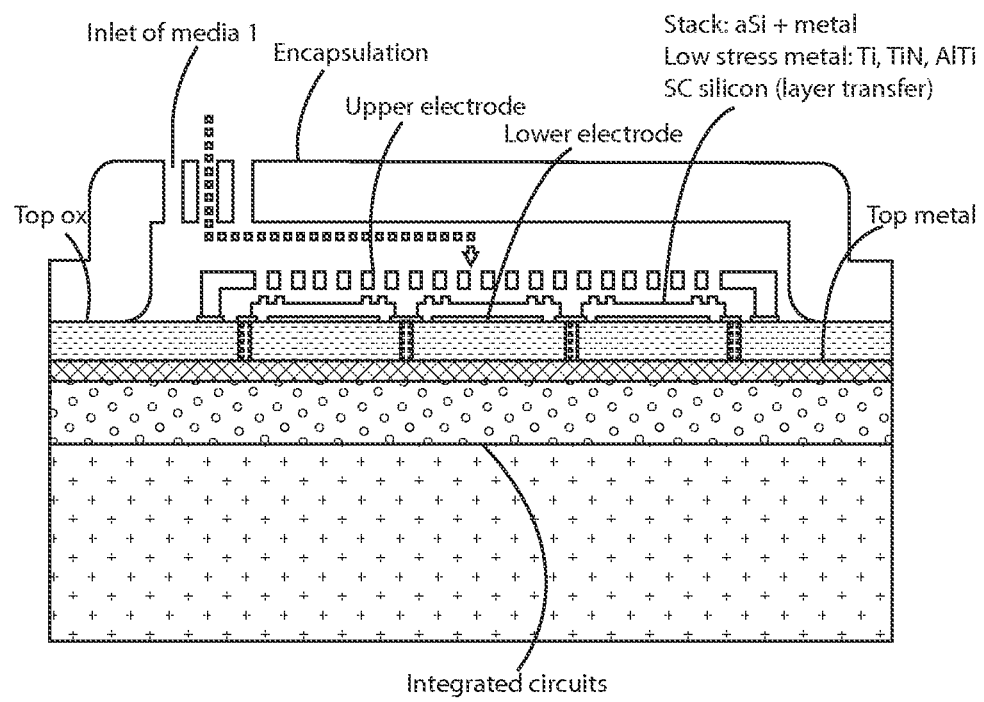
FIG. 16 is a simplified cross section diagram of components of a micromachined pressure sensor according to one embodiment of the present invention.

FIG. 16 is a simplified cross section diagram of components of a micromachined pressure sensor according to one embodiment of the present invention. As depicted, a diaphragm with corrugated springs is overlying a fully completed CMOS substrate. In one embodiment, the diaphragm is consisted with a stack of thin films such as amorphous Silicon and metal layers. In another embodiment, the diaphragm is a low stress metal thin film such as Ti, TiN, or AlTi alloy. In another embodiment, the diaphragm is a thin layer of single crystal silicon. Lower electrodes are formed at the top of the top oxide of the CMOS substrate to form a capacitor with the diaphragm. Optional upper electrodes can be formed on top of the diaphragm to form a differential output for increased sensitivity. A thick layer of insulating material with fluid inlet holes is formed on top of the diaphragm to encapsulate the pressure sensor.

Figure 17:
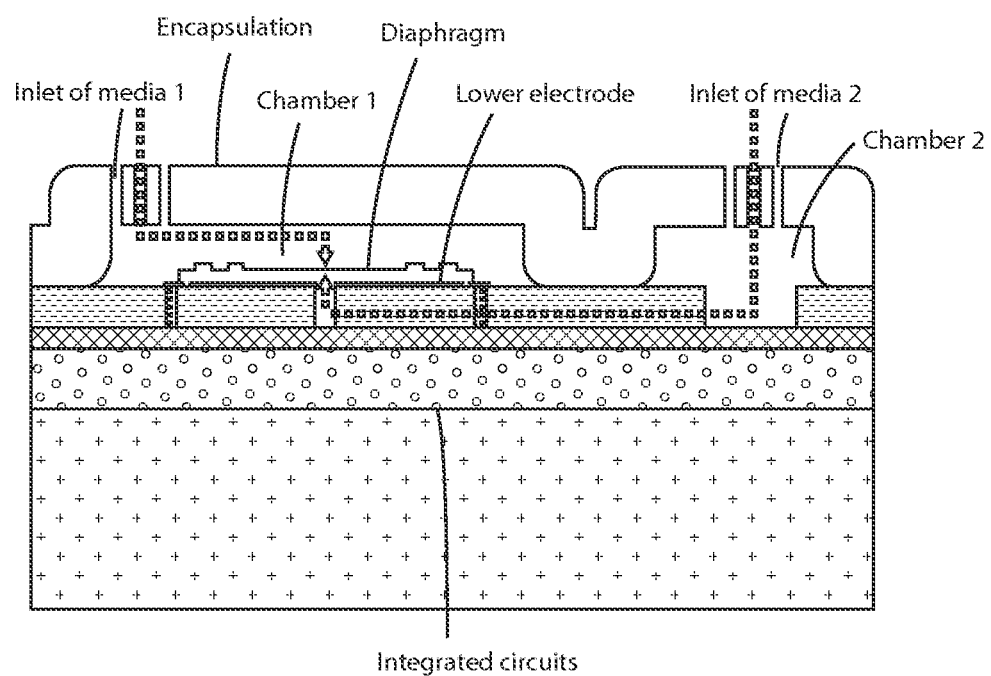
FIG. 17 is a simplified cross section diagram of components of a micromachined pressure sensor according to one embodiment of the present invention.

FIG. 17 is a simplified cross section diagram of components of a micromachined pressure sensor according to one embodiment of the present invention. As depicted, there are two separated chambers for two independent media inlets. The top oxide has embedded fluid channels that allow media 2 to flow from chamber 2 to the backside of the diaphragm in chamber 1.

Figure 18:
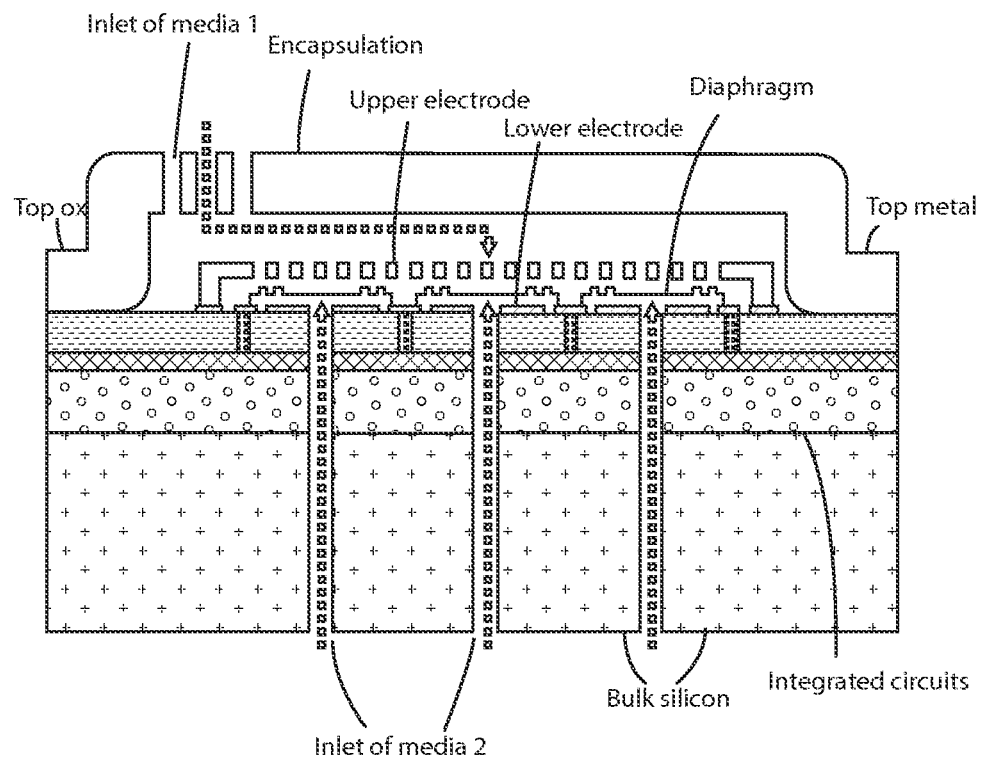
FIG. 18 is a simplified cross section diagram of components of a micromachined pressure sensor according to one embodiment of the present invention.

FIG. 18 is a simplified cross section diagram of components of a micromachined pressure sensor according to one embodiment of the present invention. As depicted, fluid channels formed within the silicon substrate to allow media 2 to flow from the bottom of the substrate to the backside of the diaphragm.

Figure 19:
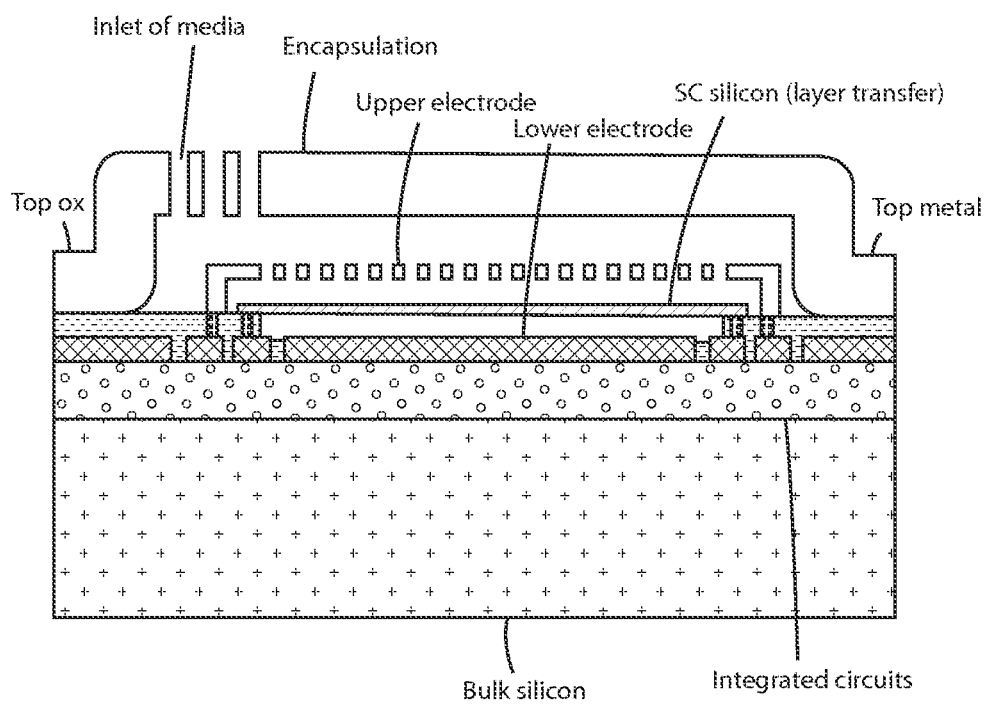
FIG. 19 is a simplified cross section diagram of components of a micromachined pressure sensor according to one embodiment of the present invention.

FIG. 19 is a simplified cross section diagram of components of a micromachined pressure sensor according to one embodiment of the present invention. As depicted, the diaphragm is made of a single crystal silicon material. In one embodiment, a SOI wafer is bond to the CMOS substrate. After removing the bulk silicon and BOX, the SOI layer is then released and becomes the diaphragm.

Figure 20:
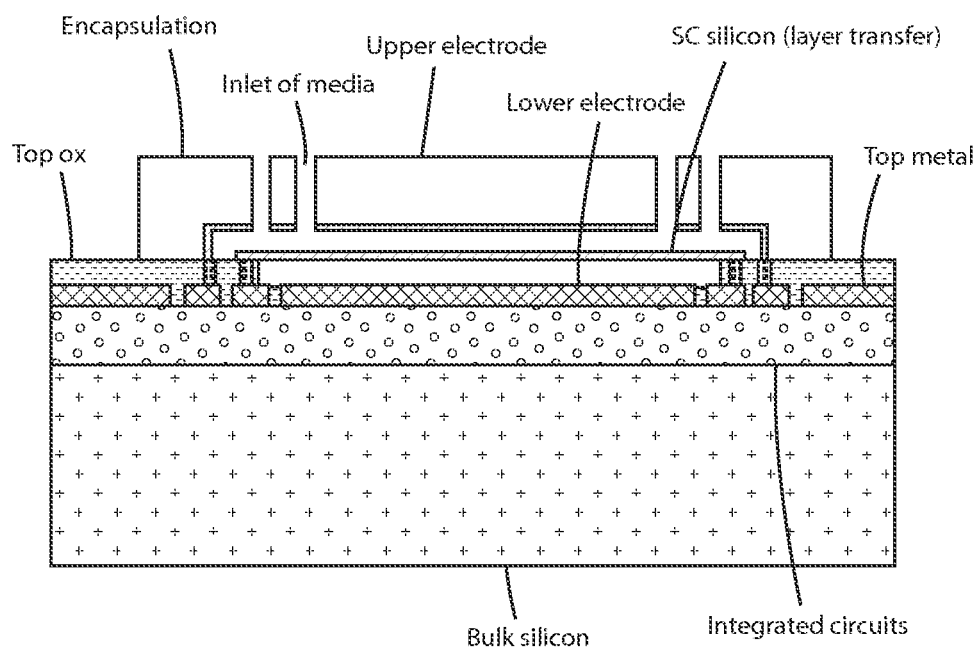
FIG. 20 is a simplified cross section diagram of components of a micromachined pressure sensor according to one embodiment of the present invention.

FIG. 20 is a simplified cross section diagram of components of a micromachined pressure sensor according to one embodiment of the present invention. As depicted, the encapsulation consisted of a thick insulation layer and a conductive layer at the bottom. The bottom conductive layer becomes the upper electrode.

Figure 21:
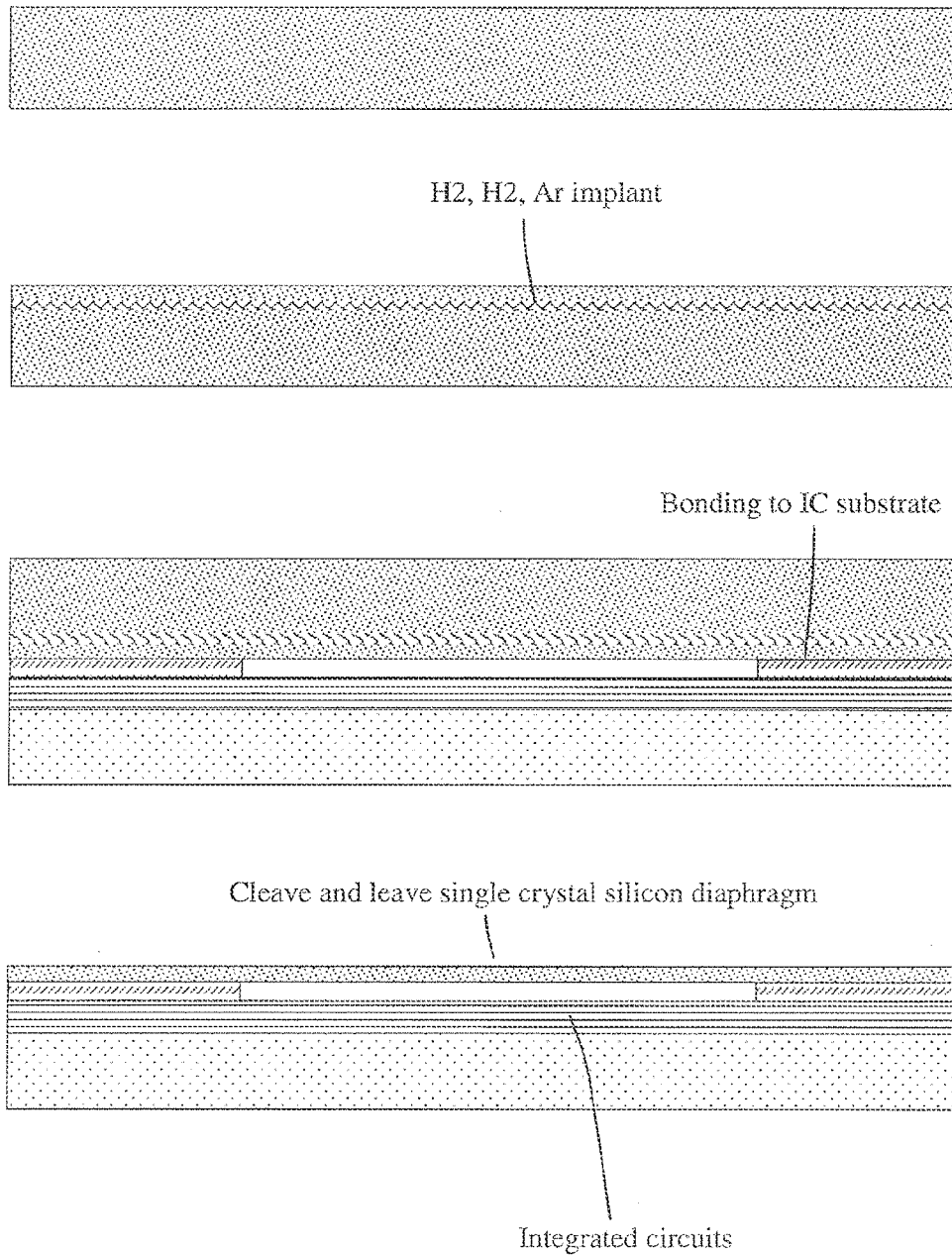
FIG. 21 is a simplified cross section diagram of fabrication process flow of a micromachined pressure sensor according to one embodiment of the present invention.

FIG. 21 is a simplified cross section diagram of fabrication process flow of a micromachined pressure sensor according to one embodiment of the present invention. As depicted, H2, He, or Argon is implanted in a desired depth in a silicon substrate. The silicon substrate is then bonded to the CMOS substrate using low temperature bonding methods such as covalent, eutectic, or other low temperature methods. Finally, a cleaving step separates the thin silicon layer from the bulk substrate. The thin silicon layer becomes the diaphragm.

Figure 22:
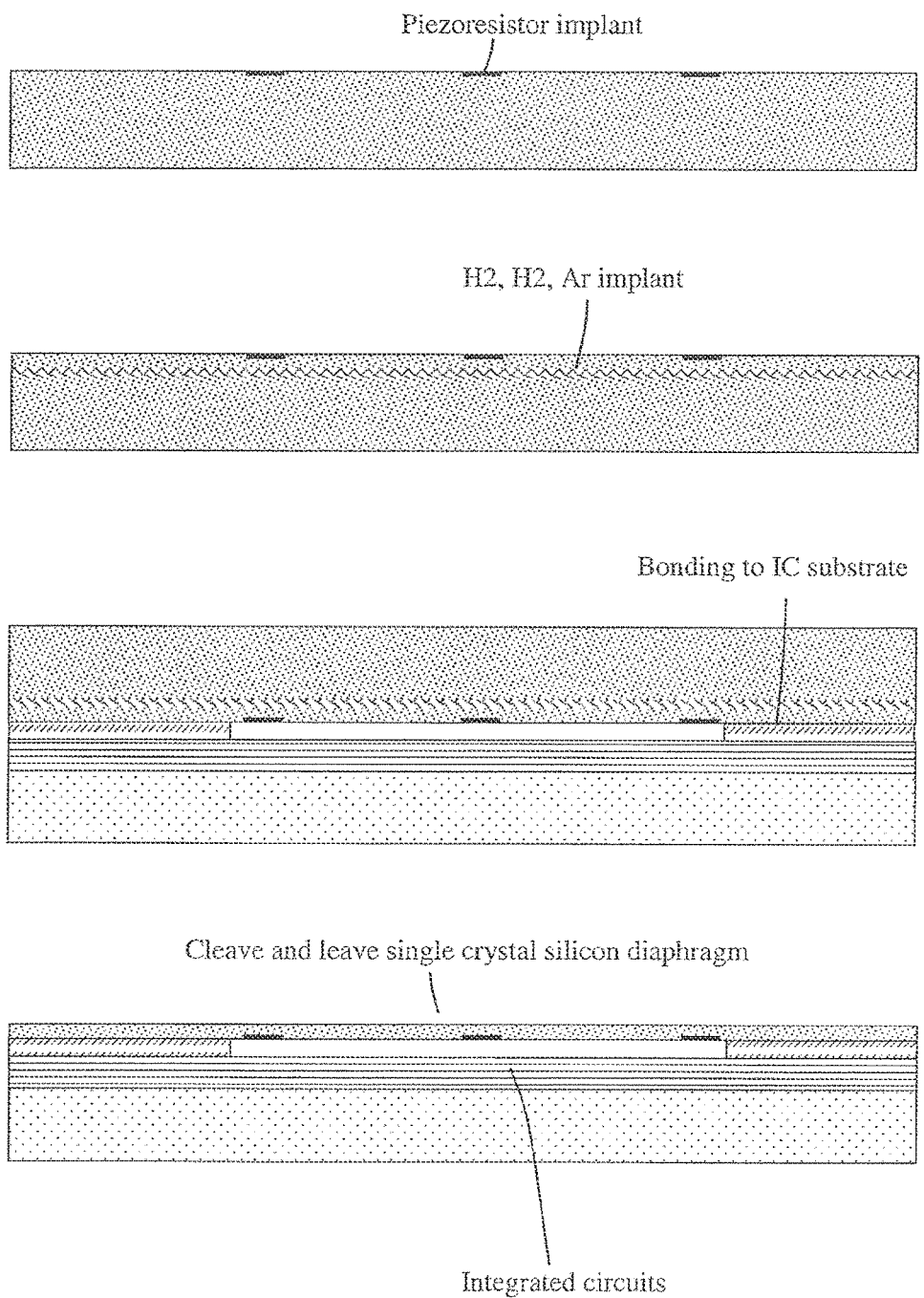
FIG. 22 is a simplified cross section diagram of fabrication process flow of a micromachined pressure sensor according to one embodiment of the present invention.

FIG. 22 is a simplified cross section diagram of fabrication process flow of a micromachined pressure sensor according to one embodiment of the present invention. As depicted, piezoresistors are implanted in a silicon substrate. H2, He, or Argon is then implanted in a desired depth in the silicon substrate. The silicon substrate is then bonded to the CMOS substrate using low temperature bonding methods such as covalent, eutectic, or other low temperature methods. Finally, a cleaving step separates the thin silicon layer from the bulk substrate. The thin silicon layer becomes the diaphragm and the embedded piezoresistors sense strains induced by the deformation of the diaphragm due to an external pressure.

In an embodiment, the present invention provides a pressure sensing device that includes a substrate having a surface region, a CMOS integrated circuit device layer overlying the surface region of the substrate, a diaphragm device having one or more surface regions overlying the CMOS integrated circuit device layer, and at least one or more spring devices spatially disposed within a vicinity of the one or more surface regions of the diaphragm device. Each of the folded spring devices is operably coupled to the one or more surface regions of the diaphragm device.

In an embodiment of the above pressure sending device, the one or more spring devices includes one or more folded spring devices. In another embodiment, the one or more spring devices are integrally formed within the one or more surface regions of the diaphragm device. In another embodiment, the one or more surface regions have a uniformity of 5 percent and less variation. In yet another embodiment, the diaphragm device is characterized by a thickness of about one micron and less. In another embodiment, the diaphragm device is made of a semiconductor material, a metal material, or a dielectric material or any combination of these.

In another embodiment, the one or more surface regions comprises an array being defined by N and M, where N and M are integers greater than 2. In another embodiment, the one or more surface regions includes at least one surface region disposed within a center region of the diaphragm and a plurality of surface regions disposed radially around the center region of the diaphragm.

In another embodiment, the above pressure sensing device also includes one or more lower electrodes operably coupled to one or more of the surface regions. In another embodiment, the pressure sensing device also includes one or more upper electrodes operably coupled to one or more of the surface regions to form one or more variable capacitor structures. In yet another embodiment, each of the one or more lower electrodes comprises one or more metal regions coupled to one or more of CMOS integrated circuits in the CMOS integrated circuit device layer. In another embodiment, each of the one or more lower electrodes has one or more metal regions overlying an upper dielectric layer provided on the CMOS integrated circuit device layer. In still another embodiment, the sensor also has one or more vent regions provided adjacent to one or more of the lower electrodes, the one or more of the vent regions extending to a cavity region within a portion substrate. In another embodiment, the pressure sensor also includes a housing member provided overlying the diaphragm device to form a cavity region between the housing member and the diaphragm device. The housing member has one or more fluid openings to allow fluid to move between the cavity and a region outside of the housing member.

According to another embodiment of the invention, a pressure sensing device includes a substrate having a surface region, a CMOS integrated circuit device layer overlying the surface region of the substrate, and a diaphragm device having one or more surface regions overlying the CMOS integrated circuit device layer. The pressure sensing device also has at least one or more spring devices spatially disposed within a vicinity of the one or more surface regions of the diaphragm device. Each of the folded spring devices is operably coupled to the one or more surface regions of the diaphragm device. The pressure sensing device also has two or more electrode devices operably coupled to each of the one or more surface regions and at least one fluid channel formed between the two or more electrode devices.

In an embodiment of the above pressure sending device, the one or more spring devices comprises one or more folded spring devices. In another embodiment, the one or more spring devices are integrally formed within the one or more surface regions of the diaphragm device. In another embodiment, the one or more surface regions have a uniformity of 5 percent and less variation. In another embodiment, the diaphragm device is characterized by a thickness of about one micron and less. In another embodiment, the diaphragm device is made of a semiconductor material, a metal material, or a dielectric material or any combination of these. In another embodiment, the one or more surface regions comprise an array being defined by N and M, where N and M are integers greater than 2.

In another embodiment, the one or more surface regions comprises at least one surface region disposed within a center region of the diaphragm and a plurality of surface regions disposed radially around the center region of the diaphragm. In another embodiment, the pressure sending device also includes one or more fluid vent regions provided within a vicinity of the two or more electrode devices. In another embodiment, the pressure sending device further includes a housing member provided overlying the diaphragm device to form a cavity region between the housing member and the diaphragm device. The housing member comprises one or more fluid openings to allow fluid to move between the fluid cavity and a region outside of the housing member. In another embodiment, the pressure sending device also includes a housing member provided overlying the diaphragm device to form a cavity region between the housing member and the diaphragm device. The housing member comprises one or more fluid openings to allow fluid to move between the fluid cavity and a region outside of the housing member. The pressure sensing device also has one or more fluid vent regions provided within a vicinity of the two or more electrode devices, the one or more vent regions being in fluid communication with the fluid cavity.

According to yet another embodiment of the invention, a pressure sensing device includes a substrate having a surface region, a CMOS integrated circuit device layer overlying the surface region of the substrate, a diaphragm device having at least a first surface region facing the CMOS integrated circuit device layer and a second surface region opposite the first surface region, and at least one or more spring devices spatially disposed within a vicinity of the first surface region of the diaphragm device, each of the folded spring devices being operably coupled to the first surface region of the diaphragm device. The pressure sensing device also has two or more electrode devices operably coupled to the first surface region and at least one fluid channel formed between the two or more electrode devices. At least one of the fluid channels is in communication with the first surface region of the diaphragm device. The pressure sensing device also has a housing member provided overlying the diaphragm device to form a cavity region between the housing member and the diaphragm device. The housing member includes one or more first fluid openings to allow fluid to move between the cavity and a first region outside of the housing member. The one or more fluid openings are in communication with the second surface region of the diaphragm.

According to another embodiment of the invention, a pressure sensing device has a substrate having a surface region and a bulk region, a CMOS integrated circuit device layer overlying the surface region of the substrate, and a diaphragm device having one or more surface regions overlying the CMOS integrated circuit device layer. The pressure sensing device also has at least one or more spring devices spatially disposed within a vicinity of the one or more surface regions of the diaphragm device, each of the folded spring devices being operably coupled to the one or more surface regions of the diaphragm device, and two or more electrode devices operably coupled to each of the one or more surface regions. The pressure sensing device also has at least one fluid channel formed between the two or more electrode devices, and a housing member provided overlying the diaphragm device to form a first cavity region between a first portion the housing member and the diaphragm device and provided to form a second cavity region between a second portion of the housing member and a portion of the CMOS integrated circuit device layer. The housing member has one or more fluid openings to allow fluid to move between the first cavity and a region outside of the housing member. Moreover, the pressure sensing device also has an isolation region between the first cavity and the second cavity, and at least one fluid communication channel coupling the at least one fluid channel and the second cavity. In an embodiment, the housing member has one or more upper electrode members, each of which is operably coupled to each of the one or more surface regions.

In another embodiment, a pressure sensing device has a substrate having a surface region and a bulk region, a CMOS integrated circuit device layer overlying the surface region of the substrate, and a diaphragm device having a first surface region facing and overlying the CMOS integrated circuit device layer and a second surface region opposite the first surface region. At least one or more spring devices are spatially disposed within a vicinity of the first surface region of the diaphragm device. Each of the folded spring devices is operably coupled to the first surface region of the diaphragm device. Two or more electrode devices are operably coupled to the first surface region. A first cavity region is provided between the first surface region and the CMOS integrated circuit device layer, the first cavity region being substantially sealed and maintains a predetermined environment. The pressure sensing device also has a housing member provided overlying the second surface region of the diaphragm device to form a second cavity region between the housing member and the diaphragm device, the housing member comprising one or more fluid openings to allow fluid to move between the second cavity and a region outside of the housing member.

In another embodiment, a pressure sensing device includes a substrate having a surface region and a bulk region, a CMOS integrated circuit device layer overlying the surface region of the substrate, and a diaphragm device having one or more surface regions overlying the CMOS integrated circuit device layer. The diaphragm device is formed from a portion of a single crystal silicon material. The pressure sensing device also has two or more electrode devices operably coupled to each of the one or more surface regions.

In an embodiment, the above pressure sensing device also has a housing overlying the diaphragm device and forming a cavity region between the housing and the diaphragm device. In an embodiment, the above pressure sensing device also has a housing overlying the diaphragm device and forming a cavity region between the housing and the diaphragm device. Additionally, one or more portions of the housing form one or more sensing electrode devices.

In another embodiment, the above pressure sensing device also has f a housing overlying the diaphragm device and forming a cavity region between the housing and the diaphragm device. The housing includes an outer region and an inner region. One or more inner portions of the inner region of the housing form one or more sensing electrode devices. In an embodiment, the single crystal silicon material is provided from a silicon on insulator substrate (SOI). In an embodiment, the single crystal silicon material is provided from a cleaved portion of single crystal silicon material.

According to an alternative embodiment, the invention provides a method of forming an integrated MEMS sensor and circuit device. The method includes providing a first semiconductor substrate having, a first surface region, one or more piezoresistor regions, and a cleave region provided between the first surface region and a bulk portion of the first semiconductor substrate. The method also includes joining the first surface region to a second surface region of a second semiconductor substrate. The second semiconductor substrate has a CMOS integrated circuit layer, a dielectric layer overlying the CMOS integrated circuit layer, and a cavity region provided within the dielectric layer. The method also includes releasing the bulk portion of the first semiconductor substrate while maintaining the first surface region attached to the second surface region.

Figure 23:
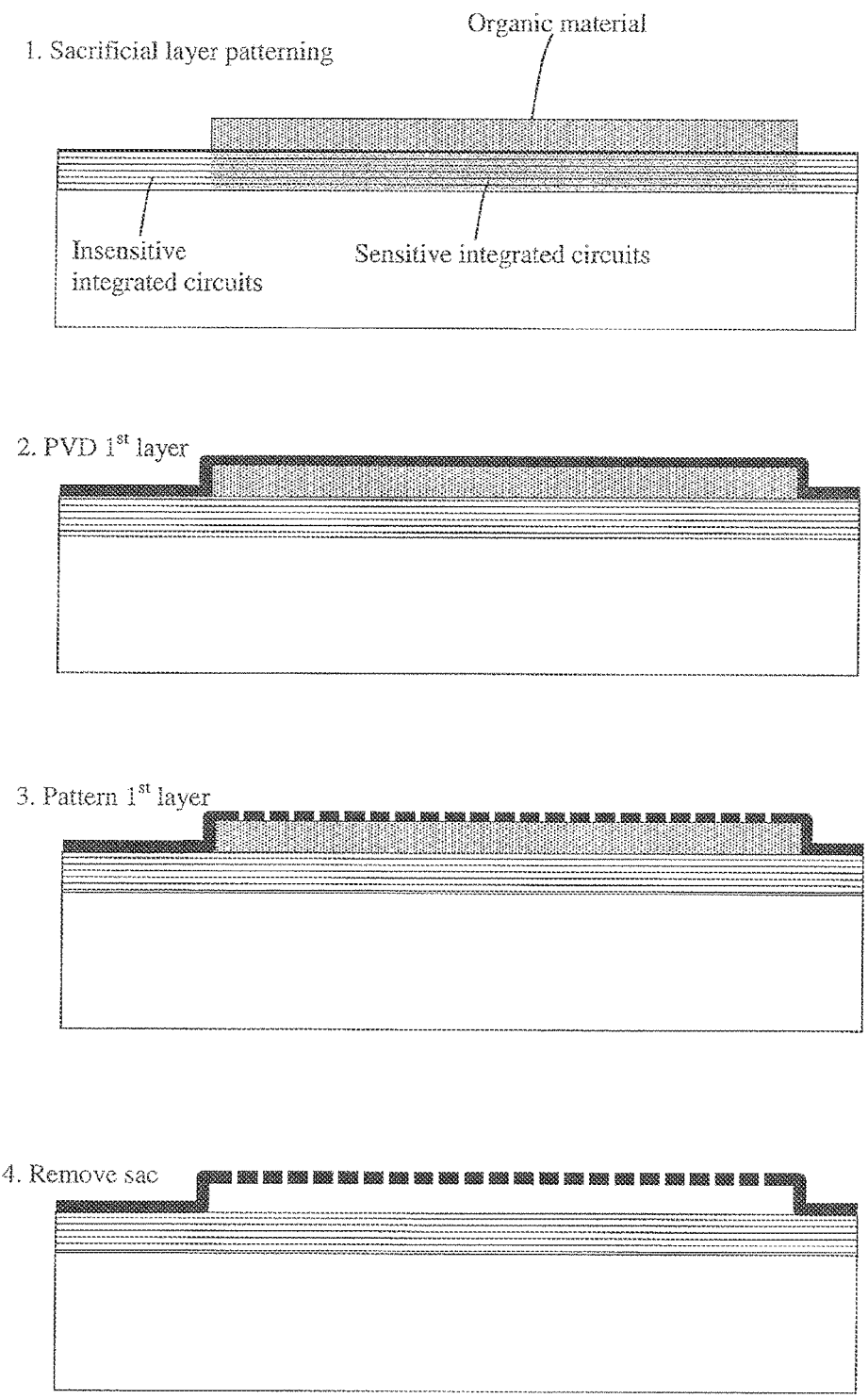
FIG. 23 is a simplified process flow of a wafer-level encapsulation of integration circuits according to one embodiment of the present invention.

FIG. 23 is a simplified process flow of a wafer-level encapsulation of Integration Circuits according to one embodiment of the present invention. As depicted, an organic sacrificial material is deposited and patterned to cover the sensitive portion of the integrated circuits. In a specific embodiment, the sacrificial material is a photo resist that is spin coated on the wafer and patterned using standard lithography methods. A thin layer of metal or amorphous silicon is then conformally deposited using a PVD process covering the surface of the wafer. A etch step is followed to form release holes in the $1^{st}$ layer. Lastly, the organic sacrificial material is then removed through the release holes by a dry O2 plasma ashing step. As depicted, the removal of the sacrificial material forms a cavity and a shell of the encapsulation.

FIG. 24 is a simplified process flow of a wafer-level encapsulation of Integration Circuits according to one embodiment of the present invention. As depicted, a $2^{nd}$ layer of the encapsulation is deposited onto the $1^{st}$ layer. The hermetic sealing methods include PVD, spin-on, or spray-on techniques. The sealing materials include metal such as Ti, TiN, amorphous silicon, spin-on-glass, spray-on-glass, or a combination of the above. The ambient during sealing is optimized and controlled to a desired spec that defines the sensor device ambient after sealing. A getter material such as Ti can be deposited as the $1^{st}$ layer of the encapsulation and activated later to achieve high vacuum and cleanness of the sensitive circuit ambient environment. After sealing the holes, an optional CVD dielectric material such as oxide or nitride can be added onto the encapsulation. Finally, a etch step opens the bond pad region and expose the bond pads for wire bonding or optional wafer bumping processes. The encapsulation and the cavity form a hermetic inert environment that shields the sensitive circuits from EM interference, noise, moisture, gas, and corrosion from the outside environment.

FIG. 25 is a simplified process flow of a wafer-level encapsulation of Integration Circuits according to one embodiment of the present invention. For applications that require thick encapsulation layer, it is desirable to form bond pads on top of the encapsulation layer instead of etching down to open the bond pads on the IC layer. As depicted, after depositing the $2^{nd}$ layer of the encapsulation, a etch step opens a region of bond pad area and expose the bond pads for a subsequent metallization step. The metal is then patterned to form bond pads for wire bonding or optional wafer bumping processes.

FIG. 26 is a simplified process flow of a wafer-level encapsulation of Integration Circuits according to one embodiment of the present invention. As depicted, an organic sacrificial material is deposited and patterned to cover the sensitive portion of the integrated circuits. The patterning also forms holes or openings in the remaining organic materials. In a specific embodiment, the sacrificial material is a photo resist that is spin coated on the wafer and patterned using standard lithography methods. A thin layer of metal or amorphous silicon is then deposited using a PVD process covering the surface of the wafer. The deposition recipe is optimized for non-conforming purpose, which has little step coverage of the sidewall of the exposed photoresist trenches. After removing the organic sacrificial material, a $2^{nd}$ layer is then deposited to form the cavity and the encapsulation by steps aforementioned. This flow uses only one mask and save process steps.

Figure 27:
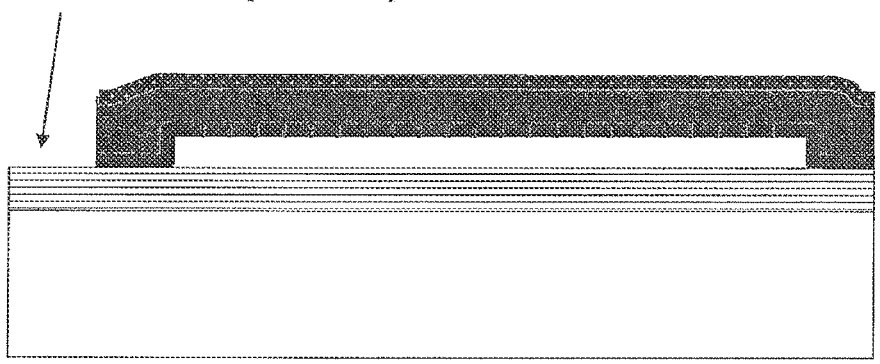
FIG. 27 is a simplified cross section of a wafer-level encapsulation of integration circuits according to one embodiment of the present invention.

FIG. 27 is a simplified cross section of a wafer-level encapsulation of Integration Circuits according to one embodiment of the present invention. As depicted, bond pad area is kept clear from encapsulation depositions by a lift-off method or using shadow mask. This eliminates the need of etching thru the encapsulation layers to expose the bond pads.

Figure 28:
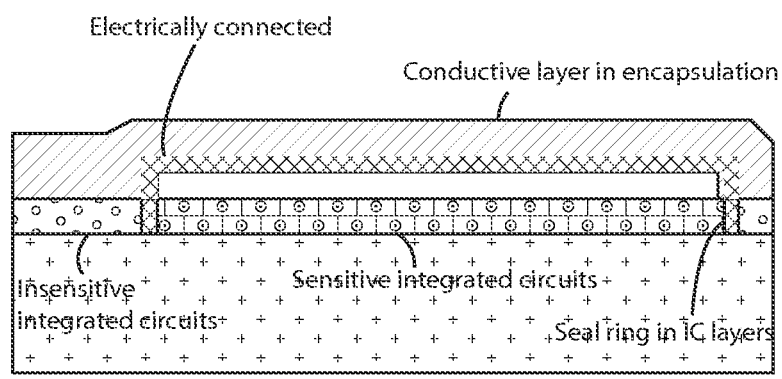
FIG. 28 is a simplified cross section of a wafer-level encapsulation of integration circuits according to one embodiment of the present invention.

FIG. 28 is a simplified cross section of a wafer-level encapsulation of Integration Circuits according to one embodiment of the present invention. As depicted, a seal ring is formed in IC layers and encircles the sensitive portion of the integrated circuits. The $1^{st}$ layer of the encapsulation is a conductive material and is electrically connected with the seal ring. As a result, the seal ring and the encapsulation form a metal cage that shields the sensitive circuits from EM interference, noise, moisture, gas, and corrosion from the environment.

In an embodiment, a packaged integrated circuit device includes a semiconductor substrate having a surface region, a first portion and a second portion. The packaged integrated circuit device also has one or more CMOS integrated circuit devices fabricated on a first portion of the semiconductor substrate, and one or more sensitive integrated circuit modules provided on a second portion of the semiconductor substrate. The packaged integrated circuit device also includes one or more dielectric layers overlying the one or more CMOS integrated circuit devices and the one or more sensitive integrated circuit modules to form a passivation structure overlying the one or more CMOS integrated circuit devices and one or more sensitive integrated circuit modules. The packaged integrated circuit device also has a void volume overlying the one or more dielectric layers within a vicinity of at least the one or more sensitive integrated circuit modules, and a barrier material overlying at least the void volume to hermetically seal the one or more sensitive integrated circuit modules while maintaining the void volume overlying the one or more dielectric layers.

In an embodiment, the above packaged integrated circuit device also includes one or more dielectric layers overlying the barrier material.

In another embodiment, the barrier material is selected from one or more semiconductor materials including amorphous silicon, polysilicon, silicon germanium, and germanium.

In another embodiment, the barrier material is selected from one or more metal materials including tungsten, platinum, titanium, titanium nitride, titanium tungsten, copper, tantalum, aluminum, or aluminum titanium alloy.

In another embodiment, the barrier material is selected from one or more dielectric materials including an oxide, a nitride, oxynitride, spin-on glass, or spray-on glass.

In another embodiment, the barrier material comprises two or more materials including a semiconductor, a metal, or a dielectric.

In another embodiment, the void volume includes air.

In another embodiment, the void volume includes an inert material.

In another embodiment, the void volume includes an inert gas.

In another embodiment, the void volume is characterized as a vacuum environment.

In another embodiment, the void volume is characterized by a dielectric constant of 1.2 and less.

In another embodiment, the one or more sensitive integrated circuit modules includes at least one or more integrated circuits including an RC timing circuit, LC timing circuit, RF circuit, or analog circuit.

According to another embodiment, a method for fabricating an integrated circuit includes providing a first semiconductor substrate having a first surface region, and forming one or more CMOS integrated circuit device provided on a CMOS integrated circuit device region overlying the first surface region. The CMOS integrated circuit device region has a CMOS surface region. The method also includes forming a dielectric layer overlying the CMOS surface region, forming a sacrificial layer overlying a portion of the dielectric layer, and forming an enclosure layer overlying the sacrificial layer. The method also includes removing the sacrificial layer via an ashing process to form a void region between the portion of the dielectric layer and the enclosure layer, and sealing the void region in a predetermined environment.

In an embodiment of the above method, the CMOS device layer is formed using a standard CMOS process from a semiconductor foundry.

In another embodiment, the enclosure layer comprises a titanium material, which is activated as a getter layer.

In another embodiment, the enclosure layer is selected from a metal, a semiconductor material, an amorphous silicon material, a dielectric layer, or a combination of these layers.

FIG. 29 is a simplified chart comparing silicon nanopillar battery to conventional battery according to one embodiment of the present invention. As shown, micromachined silicon nanopillars are adopted to replace graphite anode. The silicon nanopillar anode has high energy density since silicon holds 10× Lithium than graphite. The silicon nanopillar anode also has more surface area that can hold more active material into the electrode for fast charging and discharging. Silicon nanopillars are coated with LiCoO2 to replace LiCoO2 cathode, which more surface area that has high energy capacity and fast charging and discharging. Micromachined Silicon membrane with nanopillar to replace the conventional separator made of thin plastic. Silicon is stronger than steel and avoid damage of the separator that shorts electrodes and causes fire. In addition, nanopillar controls 'wetting' of electrolyte therefore physical contact/separation of electrodes. Silicon membrane potentially contains active IC for controlling battery operations. Modularized control of nanopillar array allows intelligent battery operation for high efficiency. As a result, silicon membrane with nanopillars has no leakage, avoids deep discharge and extends battery life.

Figure 30:
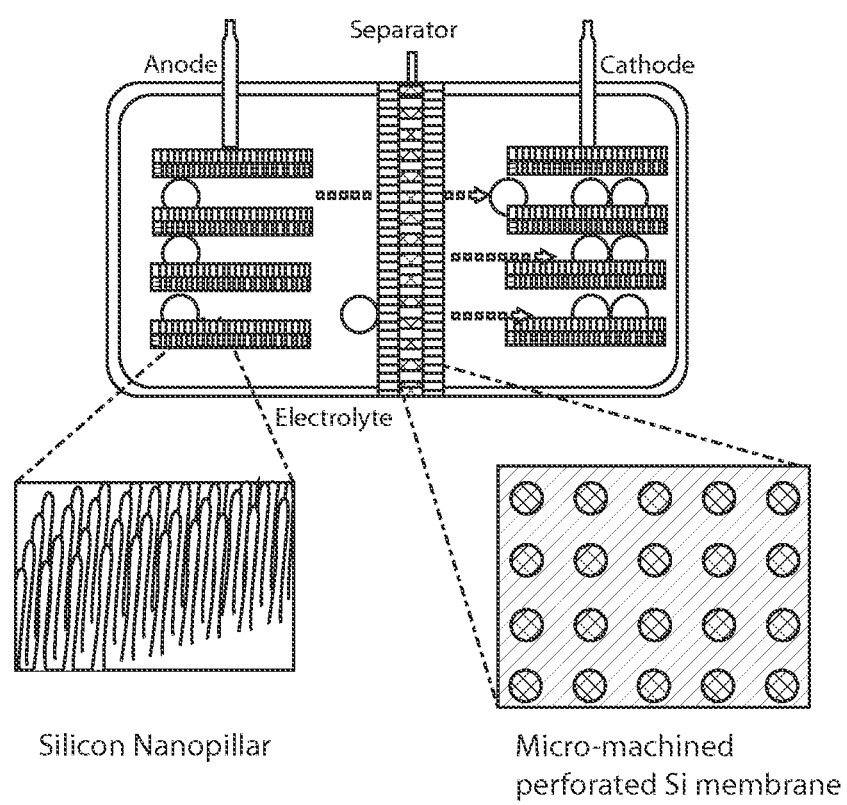
FIG. 30 is a simplified diagram of components of a silicon nanopillar battery according to one embodiment of the present invention.

FIG. 30 is a simplified diagram of components of a silicon nanopillar battery according to one embodiment of the present invention. As depicted, the anode is made of micromachined silicon nanopillars, whereas the cathode is made of silicon nanopillars coated with LiCoO2. The separator is made of micromachined silicon membrane with nanopillars. The silicon membrane has perforated holes that allow the flow of the electrolyte between the anode and cathode. The nanopillar on the silicon membrane controls 'wetting' of electrolyte and therefore physical contact/separation of electrodes.

FIG. 31 is a simplified diagram of operating modes of a silicon nanopillar battery according to one embodiment of the present invention. As depicted, in battery 'off' state, nanopillars on the silicon membrane separator are charged. As a result, the surface of the nanopillars becomes hydrophobic and electrolyte is separated from membrane. In battery partial 'on' state, a portion of the nanopillars on the silicon membrane separator are charged. As a result, the surface of the charged nanopillars becomes hydrophilic and electrolyte is 'wet' to the nanopillars and free to flow through the holes in the silicon membrane. In battery full 'on' state, all the nanopillars on the silicon membrane separator are charged. As a result, the surface of all the nanopillars becomes hydrophilic and electrolyte is 'wet' to the nanopillars and free to flow through the entire holes in the silicon membrane.

An embodiment of the invention provides an energy source. The energy source includes an anode structure comprising one or more silicon nanopillars. Each of the plurality of silicon nanopillars has a diameter of less than about 300 nanometers and a length of greater than about 0.5 microns, a cathode structure operably coupled to the anode structure, and a membrane region disposed between the anode structure and the cathode structure.

In an embodiment of the energy source described above, the anode structure comprises one or more substrate structures. At least one of the substrate structures includes the one or more silicon nanopillars.

In another embodiment, the one or more nanopillars is essentially single crystal silicon.

In another embodiment, the one or more nanopillars is essentially polysilicon.

In another embodiment, the one or more nanopillars is essentially amorphous silicon.

In another embodiment, the one or more silicon nanopillars comprises a thin oxide layer thereon.

In another embodiment, the cathode structure comprises one or more silicon nanopillars.

In another embodiment, the cathode structure comprises one or more silicon nanopillars. The one or more silicon nanopillars includes a LiCoO2 coating thereon.

another embodiment, the separator comprises a silicon substrate includes a plurality of perforations thereon. One or more of the perforations are capable of traversing one or more lithium ions therethrough.

In another embodiment, the separator includes a silicon substrate having a plurality of perforations thereon. One or more of the perforations are capable of traversing one or more lithium ions therethrough. The separating also includes a plurality of nanopillars overlying one or both of the surface regions.

In another embodiment, the separator is coupled to an electrical bias.

In another embodiment, the electrical bias is coupled to a controller provided on an integrated circuit device.

In another embodiment, the integrated circuit device is coupled to the energy source.

In another embodiment, the energy source is a battery.

In another embodiment, the energy source also includes an electrolyte operably coupled to the anode structure and the cathode structure.

In another embodiment, the separator is coupled to an electrical bias. The electrical bias is coupled to a controller provided on an integrated circuit device, and the integrated circuit device is coupled to the energy source; wherein the controller being configured to apply voltage to a selected number of the one or more nanopillars to cause the selected number of nanopillars to be an on or off state.

Figure 32:
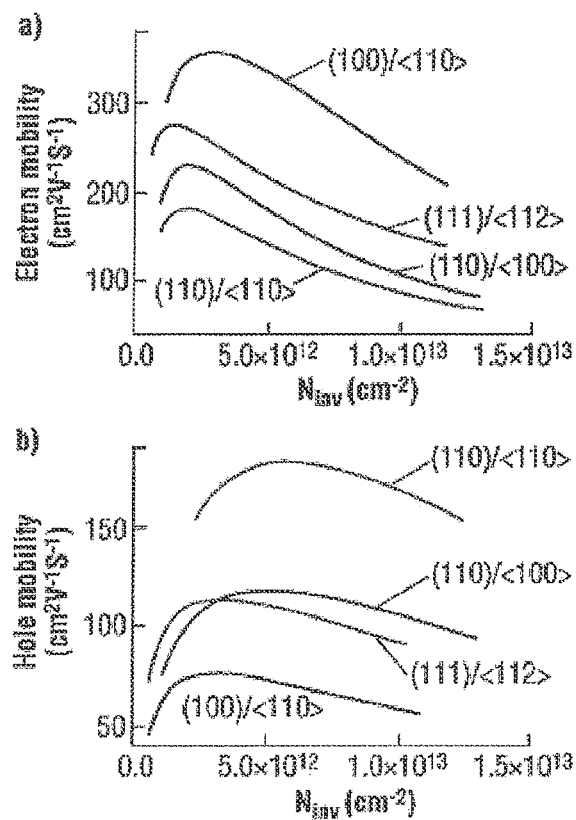
FIG. 32 illustrates electron and hole mobility for different crystal orientations.

FIG. 32 illustrates electron and hole mobility for different crystal orientations. As shown in the prior art, electron mobility is highest for a (100) silicon surface with a <110> channel direction, while hole mobility is highest for a (110) silicon surface with a <110> channel direction.

The following diagrams are merely examples, which should not unduly limit the scope of the claims herein. One of ordinary skill in the art would recognize many variations, alternatives, and modifications.

Figure 33:
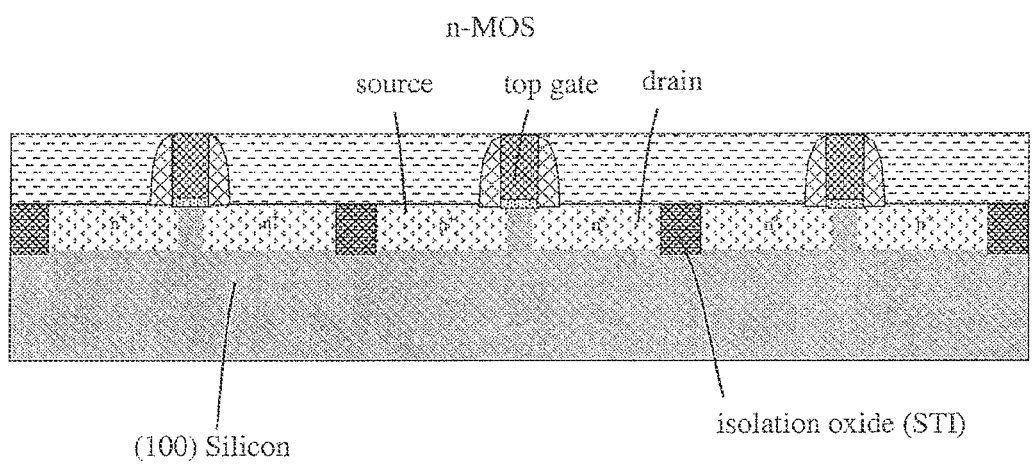
FIG. 33 is a simplified cross-sectional diagram illustrating components of n-MOS transistor device according to one embodiment of the present invention.

FIG. 33 is a simplified cross-sectional diagram illustrating components of n-MOS transistor device according to one embodiment of the present invention.

As illustrated, the n-MOS transistors are fabricated using standard CMOS processes. The starting substrate is a (100) silicon substrate which has the highest mobility for electrons. The source and drain regions can be either partially or fully depleted depending on applications. A shallow trench isolation (STI) typically oxide is formed to electrically isolate adjacent transistors. After completing poly gates, oxide is deposited followed by a CMP step to planarize the device substrate.

Figure 34:
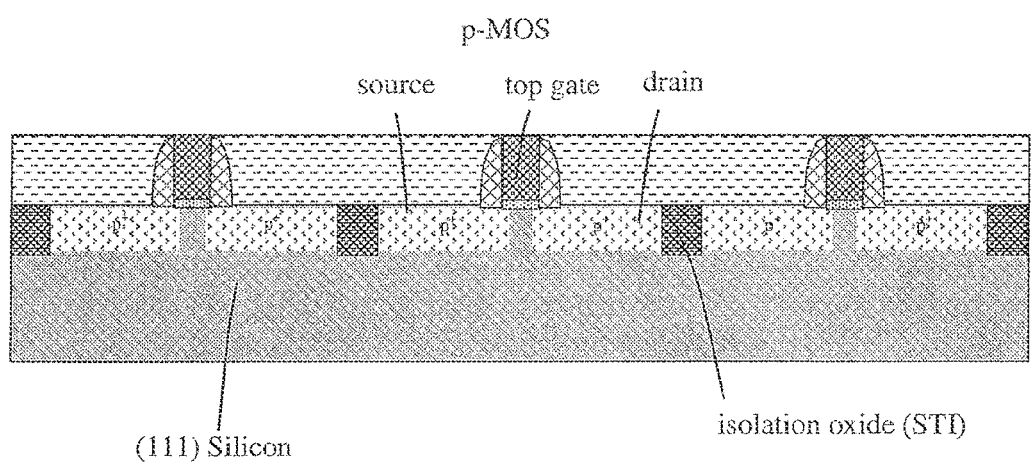
FIG. 34 is a simplified cross-sectional diagram illustrating components of p-MOS transistor device according to one embodiment of the present invention.

FIG. 34 is a simplified cross-sectional diagram illustrating components of p-MOS transistor device according to one embodiment of the present invention. As illustrated, p-MOS transistors are fabricated in a similar manner as the N transistors. The starting substrate, however, is a (110) silicon substrate which has the highest mobility for holes.

Figure 35:
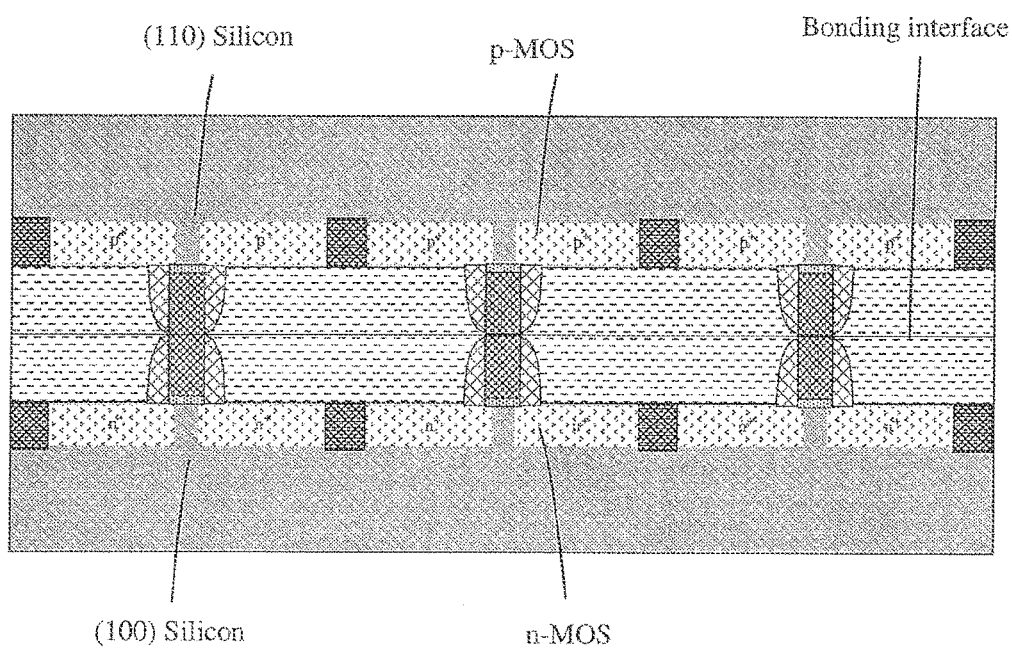
FIG. 35 is a simplified diagram illustrating a process of joining the n-MOS and p-MOS transistor substrates.

FIG. 35 is a simplified diagram illustrating a process of joining the n-MOS and p-MOS transistor substrates. The joining methods include but not limit to permanent bonding methods such as covalent, eutectic, glass frit, SOG, and fusion. Merely by way of example, a surface activation by either plasma or wet on both substrates is applied followed by a room temperature covalent bonding process.

FIG. 36 is a simplified diagram illustrating a process of thinning one of the transistor substrates. In one embodiment, the p-MOS transistor substrate is a SOI wafer and the bulk of the P transistor wafer is removed by methods such as grinding and polishing, followed by a wet or dry etch as showed stop on the BOX of the SOI. In another embodiment, the p-MOS transistor substrate is a regular wafer and the bulk of the P transistor wafer is removed by grinding and polishing while measuring the remaining silicon thickness to control the final silicon thickness. Interconnects are formed vertically after the thinning.

FIGS. 37-38 are simplified diagrams illustrating a process of fabricating three dimensional transistor devices using a cleaving method. As depicted, p-MOS transistors are implanted in a (111) silicon substrate first. After finishing high temperature process steps such as oxidation and polysilicon deposition, an implant step implants H2, He or Ar in a desired depth in the silicon substrate. The p-MOS transistor substrate is then bonded to the n-MOS transistor substrate. A cleaving step separates the bulk of the p-MOS transistor substrate and leaves a thin layer of silicon with p-MOS transistors overlying the n-MOS transistor substrate. Finally, STIs are formed between the p-MOS transistors for electrical isolation.

An embodiment of the invention provides a three-dimensional integrated circuit device that includes a first substrate having a (110) crystal orientation comprising at least one or more PMOS devices thereon; and a first dielectric layer overlying the one or more PMOS devices. The three-dimensional integrated circuit device also includes a second substrate having a (100) crystal orientation comprising at least one or more NMOS devices thereon; and a second dielectric layer overlying the one or more NMOS devices. The three-dimensional integrated circuit device also has an interface region coupling the first dielectric layer to the second dielectric layer to form a hybrid structure including the first substrate overlying the second substrate.

In an embodiment of the above three-dimensional integrated circuit device, the interface region characterized by a bonding material.

In another embodiment, the first substrate is single crystal silicon material.

In another embodiment, the second substrate is single crystal silicon material.

In another embodiment, the first substrate is cleaved.

In another embodiment, the second substrate is cleaved.

In another embodiment, the first substrate and the second substrate form a vertical integrated CMOS integrated circuit device.

Figure 39:
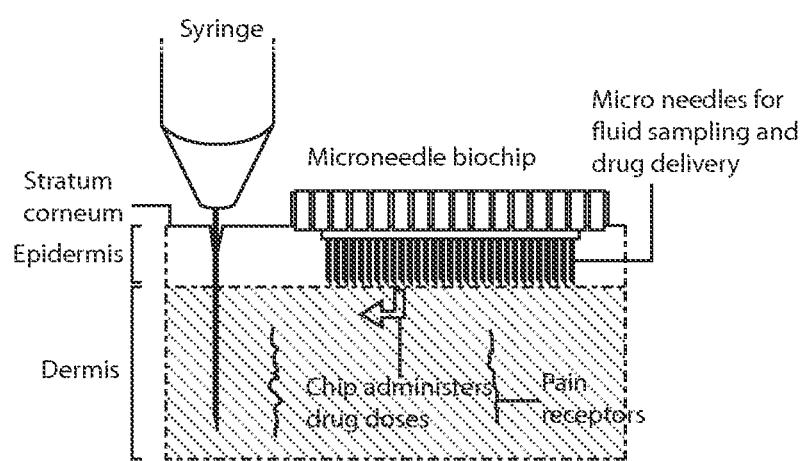
FIG. 39 is a simplified cross section diagram of a microneedle biochip according to one embodiment of the present invention.

FIG. 39 is a simplified cross section diagram of a microneedle biochip according to one embodiment of the present invention. As depicted, the microneedles penetrate only the Stratum Corneum and Viable Epidermis layers, whereas the conventional macro needle penetrates to Dermis layer where pain receptor nerves reside. The microneedle chip samples body analyte through extraction of interstitial fluid through the microneedles for on-chip sensing. The microneedles are also used for real-time drug delivery based on the sensing results.

Figure 40:
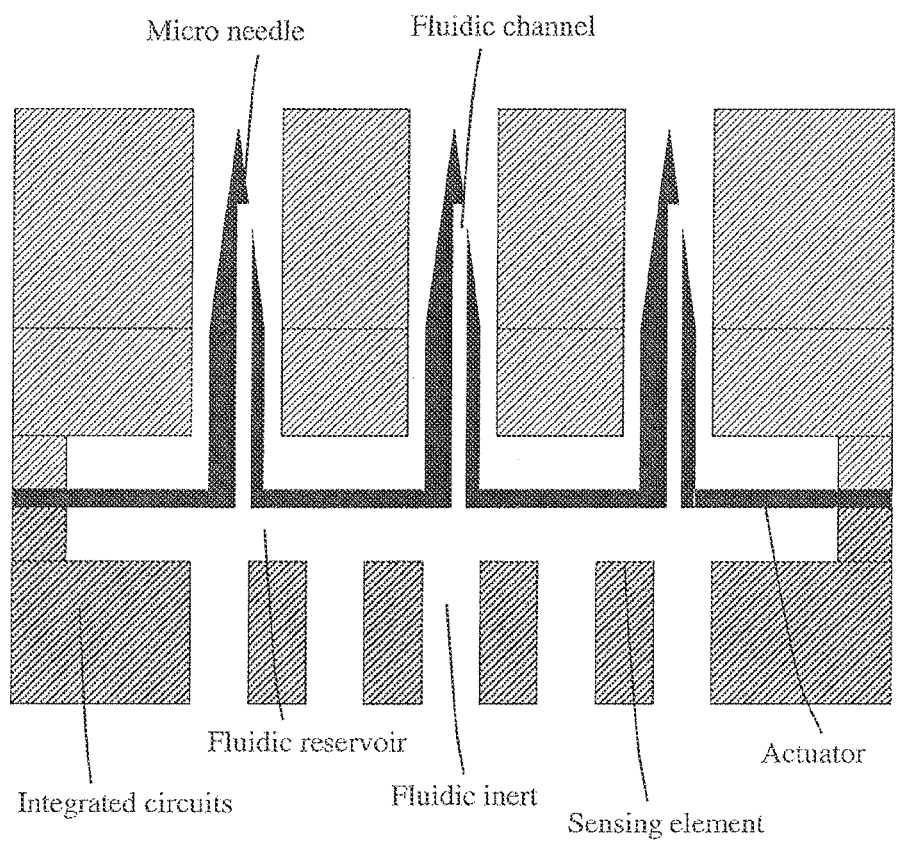
FIG. 40 is a simplified cross section diagram of components of a microneedle biochip according to one embodiment of the present invention.

FIG. 40 is a simplified cross section diagram of components of a microneedle biochip according to one embodiment of the present invention. As depicted, the microneedle device is fabricated on an IC substrate. The microneedles are sharp tips with micro fluidic channels inside. The microneedles are coupled to actuators that move microneedles in out-of-plane movement. Fluidic reservoir is fabricated in the IC substrate as sample chamber for sensing and storage for fluidic medicine for drug delivery. Fluidic channels are fabricated in the IC substrate for controlling fluidic medicine. Sensing elements are built on-chip to detect body analyte extracted by the microneedles. In one embodiment, glucose from the interstitial fluid of the epidermis diffuses through microneedles into the reservoir. An integrated enzyme-based electrochemical glucose sensor measures the glucose concentration. On-chip integrated circuits enable real-time sensing and intelligent drug delivery.

Figure 41:
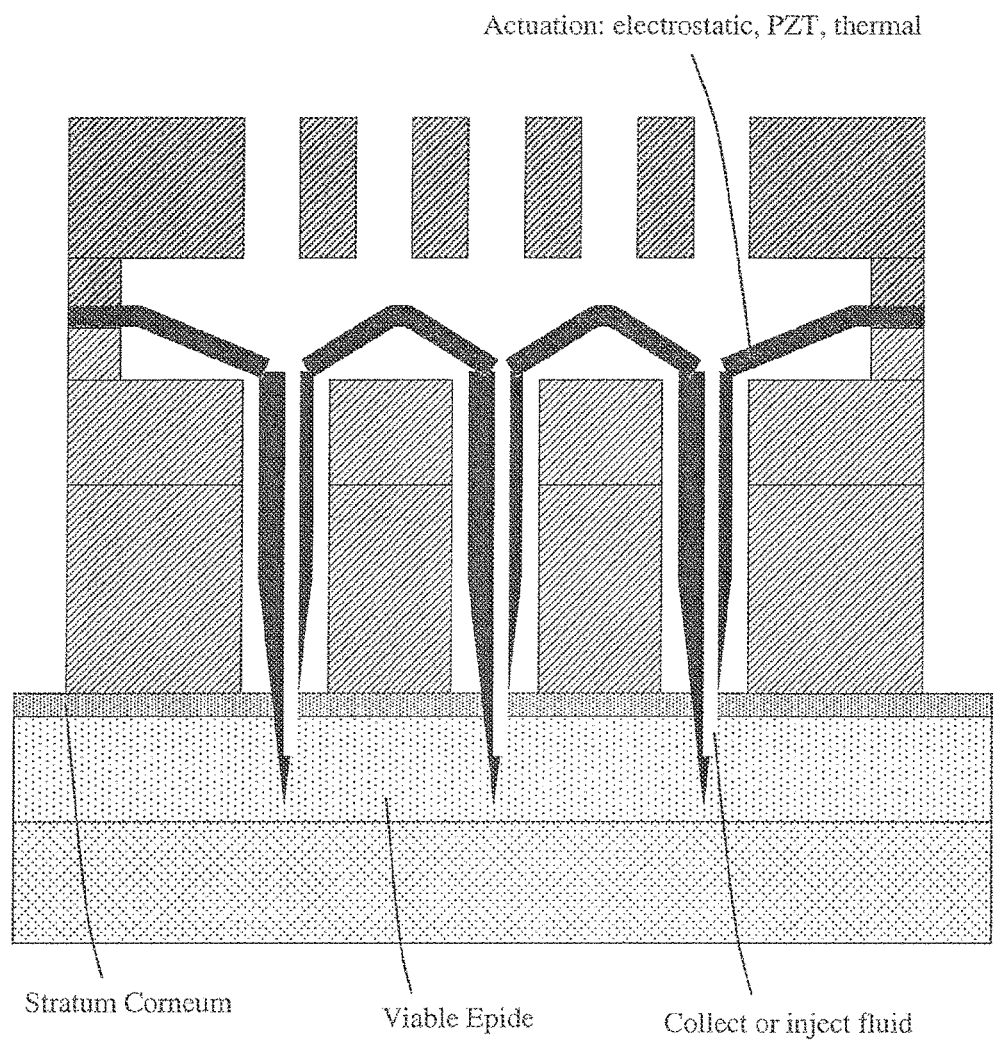
FIG. 41 is a simplified cross section diagram of components of a microneedle biochip according to one embodiment of the present invention.

FIG. 41 is a simplified cross section diagram of components of a microneedle biochip according to one embodiment of the present invention. As depicted, the microneedle device is in contact with a skin. The actuators move the microneedles in an out-of-plane displacement that penetrate into the Stratum Corneum and Viable Epide layers. The actuation methods include not limited to: electrostatic, PZT, thermal. The micro fluidic channels in the microneedles extract interstitial fluid for on-chip sensing and are also used for drug delivery into the body. The depth of penetration can be adjusted intelligent by the on-chip integrated circuits for various skin thickness and sensing or drug delivery applications.

An embodiment of the invention provides an integrated biosensor and circuit device that includes a semiconductor substrate comprising a surface region, a CMOS integrated circuit layer overlying the surface region, and one or more dielectric layers overlying the CMOS integrated circuit layer. The integrated biosensor and circuit device also includes a fluid chamber region overlying the CMOS integrated circuit layer, and one or more needle devices in communication with the fluid chamber region. The one or more needle devices overlies the CMOS integrated circuit layer. Each of the needle devices has fluid channel therein, which extends from a base region to a vicinity of a tip region. One or more sensing devices are coupled to the one or more needle devices. The one or more sensing devices are provided from the CMOS integrated circuit device layer.

In an embodiment of the integrated biosensor and circuit device, the tip region ranges from a few nanometers to about microns.

In another embodiment, the one or more sensing devices provided in the fluid chamber.

In another embodiment, the tip is made of a material selected from silicon, titanium nitride, titanium, or stainless steel.

In another embodiment, the one or more needle devices comprises a plurality of needle devices configured in an N by M array, where M is an integer greater than 2.

In another embodiment, the integrated biosensor and circuit device further includes a pump device in communication with the fluid chamber.

In another embodiment, the integrated biosensor and circuit device further includes a drug source in communication with the fluid chamber.

In another embodiment, the integrated biosensor and circuit device further includes one or more actuator devices in fluid communication with the fluid chamber. The one or more actuator devices are coupled to one or more drive devices. The one or more drive devices are selected from at group consisting of one or more electrodes, one or more PZT devices, one or more diaphragm devices, one or more thermal devices, or one or more magnetic devices.

It is also understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A method for fabricating a three-dimensional integrated circuit device, the method comprising:
   providing a first substrate having a first crystal orientation;
   forming at least one or more PMOS devices overlying the first substrate;
   forming a first dielectric layer overlying the one or more PMOS devices;
   providing a second substrate having a second crystal orientation;
   forming at least one or more NMOS devices overlying the second substrate;
   forming a second dielectric layer overlying the one or more NMOS devices; and
   coupling the first dielectric layer to the second dielectric layer to form a hybrid structure including the first substrate overlying the second substrate;
   forming a third dielectric layer overlying the hybrid structure; and
   forming a pressure sensing device overlying the third dielectric layer,
   wherein forming the pressure sensing device comprising:
      forming a diaphragm device having a first surface region facing and overlying the hybrid structure and a second surface region opposite the first surface region;

forming at least one or more folded spring devices spatially disposed within a vicinity of the first surface region of the diaphragm device, each of the folded spring devices being operably coupled to the first surface region of the diaphragm device;

forming two or more electrode devices operably coupled to the first surface region;

forming a first cavity region provided between the first surface region and the hybrid structure, the first cavity region being substantially sealed and maintaining a predetermined environment; and forming a housing member provided overlying the second surface region of the diaphragm device to form a second cavity region between the housing member and the diaphragm device, the housing member comprising one or more fluid openings to allow fluid to move between the second cavity and a region outside of the housing member.

2. The method of claim 1 wherein the first crystal orientation comprises a (110) crystal orientation or a (111) crystal orientation.

3. The method of claim 1 wherein the second crystal orientation comprises a (100) crystal orientation.

4. The method of claim 1 wherein the coupling of the first and second dielectric layer comprises a covalent, eutectic, glass frit, SOG, thermal compression, or fusion bonding process.

5. The method of claim 1 further comprising forming one or more trench isolation (STI) oxides formed to isolate adjacent transistors.

6. The method of claim 1 further comprising thinning the first substrate via a grinding, polishing, etching, or cleaving process.

7. The method of claim 1 wherein the forming of the one or more PMOS transistors comprises an implanting process in a (111) silicon substrate.

8. The method of claim 7 wherein the implanting process comprises implanting $H_2$, He, or Ar in a desired depth in the silicon substrate.

9. The method of claim 1 further comprising forming one or more vertical interconnects within one or more portions of the hybrid structure.

10. A method for forming a three-dimensional integrated circuit device comprising:

forming a first substrate having a first crystal orientation and including:
at least one or more PMOS device thereon; and
a first dielectric layer overlying the one or more PMOS devices;

forming a second substrate having a second crystal orientation, and including:
at least one or more NMOS devices thereon; and
a second dielectric layer overlying the one or more NMOS devices;

coupling the first dielectric layer to the second dielectric layer to form a hybrid structure including the first substrate overlying the second substrate; and forming a pressure sensing device overlying the hybrid structure, wherein forming the pressure sensing device comprising:
forming a diaphragm device having at least a first diaphragm surface region facing the hybrid structure and a second diaphragm surface region opposite the first surface region;

forming one or more spring devices spatially disposed within a vicinity of the first diaphragm surface region of the diaphragm device, each of the spring devices being operably coupled to the first diaphragm surface region of the diaphragm device;

forming two or more electrode devices operably coupled to the first diaphragm surface region;

forming at least one fluid channel formed between the two or more electrode devices, at least one of the fluid channels being in communication with the first diaphragm surface region of the diaphragm device; and forming a housing member provided overlying the diaphragm device to form a cavity region between the housing member and the diaphragm device, the housing member comprising one or more first fluid openings to allow fluid to move between the cavity and a first region outside of the housing member, the one or more fluid openings being in communication with the second diaphragm surface region of the diaphragm.

11. The method of claim 10 wherein the first crystal orientation comprises a (110) crystal orientation or a (111) crystal orientation.

12. The method of claim 10 wherein the second crystal orientation comprises a (100) crystal orientation.

13. The method of claim 10 wherein the coupling of the first and second dielectric layer comprises a covalent, eutectic, glass frit, SOG, thermal compression, or fusion bonding process.

14. The method of claim 10 further comprising forming one or more trench isolation (STI) oxides formed to isolate adjacent transistors.

15. The method of claim 10 further comprising thinning the first substrate via a grinding, polishing, etching, or cleaving process.

16. The method of claim 10 wherein the forming of the one or more PMOS transistors comprises an implanting process in a (111) silicon substrate.

17. The method of claim 10 wherein the implanting process comprises implanting $H_2$, He, or Ar in a desired depth in the silicon substrate.

18. The method of claim 10 wherein further comprising forming one or more vertical interconnects within one or more portions of the hybrid structure.

* * * * *